(12) United States Patent
Cho et al.

(10) Patent No.: US 8,247,378 B2
(45) Date of Patent: Aug. 21, 2012

(54) HOMING PEPTIDE FOR TUMOR VASCULATURE

(75) Inventors: Chi Hin Cho, Hong Kong (CN); Zhi Jie Li, Hong Kong (CN)

(73) Assignee: The Chinese University of Hong Kong, Shatin, New Territories, Hong Kong SAR (CN)

( * ) Notice: Subject to any disclaimer, the term of this patent is extended or adjusted under 35 U.S.C. 154(b) by 245 days.

(21) Appl. No.: 12/844,018

(22) Filed: Jul. 27, 2010

(65) Prior Publication Data

US 2011/0027176 A1     Feb. 3, 2011

Related U.S. Application Data

(60) Provisional application No. 61/229,606, filed on Jul. 29, 2009.

(51) Int. Cl.
*A61K 38/00* (2006.01)

(52) U.S. Cl. ........... 514/19.2; 435/4; 530/324; 530/325; 530/326; 530/327; 530/328

(58) Field of Classification Search ................ None
See application file for complete search history.

(56) References Cited

FOREIGN PATENT DOCUMENTS

CN     1580075     2/2005

OTHER PUBLICATIONS

International Search Report dated Nov. 4, 2010, issued in related International Patent Application No. PCT/CN2010/001149, filed Jul. 29, 2010.
Ick, C.K., "A New homing peptide toward tumor vaseculature shows tissue specificity," Jul. 23, 2008, Journal of Controlled Release, vol. 131, No. 2, pp. 85.
Hui, X.L. et al., "Specific targeting of the vasculature of gastric cancer by a new tumor-homing peptide CGNSNPKSC," Jul. 23, 2008, Journal of Controlled Release, vol. 131, No. 2, pp. 86-93.

*Primary Examiner* — Sheela J Huff
(74) *Attorney, Agent, or Firm* — Kilpatrick Townsend & Stockton LLP

(57) ABSTRACT

This invention provides for a 9 mer peptide (CTPSPFSHC SEQ ID NO:1) that selectively binds to the tumor vasculature supporting tumors of the alimentary canal. The homing peptide has both diagnostic and therapeutic uses.

22 Claims, 24 Drawing Sheets

A

B

A

B

SEQUENCE LISTING

<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: synthetic alimentary tumor vascular homing
      peptide, targeting or homing domain TCP-1

```
<400> SEQUENCE: 1

Cys Thr Pro Ser Pro Phe Ser His Cys
 1               5

<210> SEQ ID NO 2
<211> LENGTH: 9
<212> TYPE: PRT
<213> ORGANISM: Artificial Sequence
<220> FEATURE:
<223> OTHER INFORMATION: synthetic FITC-conjugated alimentary tumor
      vascular homing peptide, FITC-conjugated targeting
      or homing domain TCP-1
<221> NAME/KEY: MOD_RES
<222> LOCATION: (1)...(1)
<223> OTHER INFORMATION: Cys modified by FITC

<400> SEQUENCE: 2

Cys Thr Pro Ser Pro Phe Ser His Cys
 1               5

<210> SEQ ID NO 3
<211> LENGTH: 9
<212> TYPE: PRT
<213> ORGANISM: Artificial Sequence
<220> FEATURE:
<223> OTHER INFORMATION: synthetic FITC-conjugated negative control
      peptide
<221> NAME/KEY: MOD_RES
<222> LOCATION: (1)...(1)
<223> OTHER INFORMATION: Cys modified by FITC

<400> SEQUENCE: 3

Cys Val Gln Thr Ala Gln Leu Leu Cys
 1               5

<210> SEQ ID NO 4
<211> LENGTH: 24
<212> TYPE: DNA
<213> ORGANISM: Artificial Sequence
<220> FEATURE:
<223> OTHER INFORMATION: synthetic PCR amplification forward primer

<400> SEQUENCE: 4
agcaagctga taaaccgata caat                                          24

<210> SEQ ID NO 5
<211> LENGTH: 24
<212> TYPE: DNA
<213> ORGANISM: Artificial Sequence
<220> FEATURE:
<223> OTHER INFORMATION: synthetic PCR amplification reverse primer

<400> SEQUENCE: 5
taccgtaaca ctgagtttcg tcac                                          24

<210> SEQ ID NO 6
<211> LENGTH: 7
<212> TYPE: PRT
<213> ORGANISM: Artificial Sequence
<220> FEATURE:
<223> OTHER INFORMATION: synthetic proapoptotic peptide, apoptosis
      inducing peptide

<400> SEQUENCE: 6

Lys Leu Ala Lys Leu Ala Lys
 1               5
```

-continued

```
<210> SEQ ID NO 7
<211> LENGTH: 9
<212> TYPE: PRT
<213> ORGANISM: Artificial Sequence
<220> FEATURE:
<223> OTHER INFORMATION: synthetic negative control peptide

<400> SEQUENCE: 7

Cys Val Gln Thr Ala Gln Leu Leu Cys
 1               5
```

HOMING PEPTIDE FOR TUMOR VASCULATURE

CROSS-REFERENCES TO RELATED APPLICATIONS

This application claims the benefit under 35 U.S.C. §1.119 (e) of U.S. provisional Application No. 61/229,606, filed Jul. 29, 2009, the contents of which are incorporated by reference in the entirety.

BACKGROUND OF THE INVENTION

Tumors of the alimentary canal, especially, colorectal cancer (CRC) is the third most common malignancy and the fourth most frequent cause of cancer deaths worldwide. The 5-year overall survival rate for all stages is 40-60%, because early diagnosis is difficult and more than half of the patients with CRC ultimately develop locoregional recurrence and/or distant metastases. Furthermore current chemotherapy is tissue non-specific and usually produces severe systemic toxicities. Therefore, it is essential to improve methods for early diagnosis and further to identify novel therapeutic strategies selectively targeting cancer tissues of the alimentary canal.

It is well-known that tumors cannot grow without a blood supply. To this end, growth of new blood vessels from existing ones, i.e. angiogenesis is necessary for tumor growth. Ample evidence has shown that tumor vasculature expresses unique markers that distinguish it from normal vasculature both structurally and physiologically. Vascular cells are genetically stable. Thus anti-angiogenesis therapies provide a promising approach for treatment of tumors of the alimentary canal with higher efficacy and lower toxicity than existing therapies.

The current invention arose from in vivo biopanning with a phage library. In vivo phage display technology has been successfully used as a tool to identify peptides that selectively home to tumor vasculatures. Homing peptides selected by this method have been used as carriers of drugs and imaging agents for cancers.

BRIEF SUMMARY OF THE INVENTION

This invention provides for a 9 mer peptide (CTPSPFSHC SEQ ID NO:1) that selectively binds to the tumor vasculature supporting tumors of the alimentary canal. The homing peptide has both diagnostic and therapeutic uses.

The homing peptide of this invention was discovered by in vivo biopanning with phage incorporating a library of random peptides, We used the technology to identify peptides that recognize the vasculatures of orthotopic colorectal cancer established in the BALB/C mice. A CX7C library displayed on M13 phage was injected into the mouse with the orthotopic colorectal cancer through tail vein to accomplish the selection. After four rounds of in vivo selection, a specific phage (CTPSPFSHC-phage) was selected by this manner. This phage was found to selectively home in upon the colon cancer tumor 10-90 fold more than other organs. The synthetic peptide displayed by the phage was shown to inhibit the homing ability of the phage to tumor mass when co-injected into the animals with the CTPSPFSHC-(TCP-1)-phage. Meanwhile, immunostaining analysis indicated that TCP-1 phage and the synthetic peptide labeled by FITC could be colocalized with the vasculature marker CD31 and accumulated in the colorectal cancer tissue, but not in normal control tissues. Similar findings were observed in human colorectal cancer tissues. This peptide is useful for the identification of colon cancer and as a carrier for an anti-cancer agent targeting the vasculature of tumors. To this latter objective, systemic administration with a chimeric peptide consisting of the homing peptide TCP-1 linked to a proapoptotic peptide $_D$(KLAK-LAK)$_2$ caused more expression of caspase 3, a marker of apoptosis, in the tumor vasculatures than the control either with the uncoupled TCP-1 peptide or with vehicle.

This invention provides for an alimentary tumor vascular homing protein comprising at least one copy of a targeting or homing domain consisting of CTPSPFSHC (SEQ ID NO:1) designated TCP-1. The homing protein may have a molecular weight of between 1 and 100 kDa. The protein may have repeat copies of TCP-1 of between 2 and 10 or greater. The homing protein is optionally mixed with pharmaceutically acceptable ingredients to form a pharmaceutical composition. The pharmaceutical composition may be sterile and may be maintained in a buffer at a physiological pH of between 6 and 8. The protein may be prepared as a lyophilized powder or in a sterile aqueous fluid.

The invention further provides for the above described homing protein to be functionalized with either detectable labels or therapeutic agents. The detectable feature may comprise a detectable moiety selected from the group consisting of fluorophore, a radiopaque dye, a magnetic imaging contrast agent and a radiolabel. The therapeutic feature may be an anti-cancer agent selected from the group consisting of alkylating agents, bifunctional alkylating agents, non-steroidal aromatase inhibitors, immunotherapeutic agents, nitrosourea compounds, antimetabolites, antitumor antibiotics, mitotic inhibitors, radiation, topoisomerase I inhibitors, and antiestrogens. The above described functional moieties may be directly or indirectly bound or fused to the TCP-1 containing protein. The functional moiety may be fused to the homing protein via a covalent bond or bound through an ionic bond.

The invention further comprises methods of detecting tumors of the alimentary canal using homing proteins comprising TCP-1 domains where the methods comprise contacting the alimentary canal of the mammal hosting a solid tumor located in its alimentary canal and surrounded by tumor-induced vasculature with an amount of an alimentary tumor vascular homing protein comprising at least one copy of a domain consisting of CTPSPFSHC (SEQ ID NO:1) said protein linked to a detectable moiety where the amount is sufficient to detect the tumor-induced vascular tissue surrounding the tumor; and detecting the homing protein in the tumor-induced vascular tissue. The homing proteins used to detect tumors may be presented in any of the embodiments described above for the TCP-1 compositions, including the above described detectable moieties. The method further comprises contacting the tumor with the homing protein via intravenous injection. The tumor may be in any portion of the alimentary canal including the esophagus, stomach and intestine.

The invention further provides for a method of reducing a solid tumor load of a patient hosting a solid tumor located in its alimentary canal and surrounded by tumor-induced vasculature, said method comprising the steps of administering an amount of a therapeutic agent comprising the alimentary tumor vascular homing protein described above wherein the protein is linked to an anti-cancer agent capable of reducing the tumor load of the patient and wherein the amount of therapeutic agent administered to the patient is sufficient to reduce the tumor load of the patient. The method is preferably directed to treating a carcinoma. The preferred anti-cancer agents are listed above.

It is an objective of this invention to provide improved methods of detecting and treating solid tumors of the alimentary canal by identifying peptides that can selectively target the vasculature of the tumors.

DETAILED DESCRIPTION OF THE INVENTION

Figure 1:
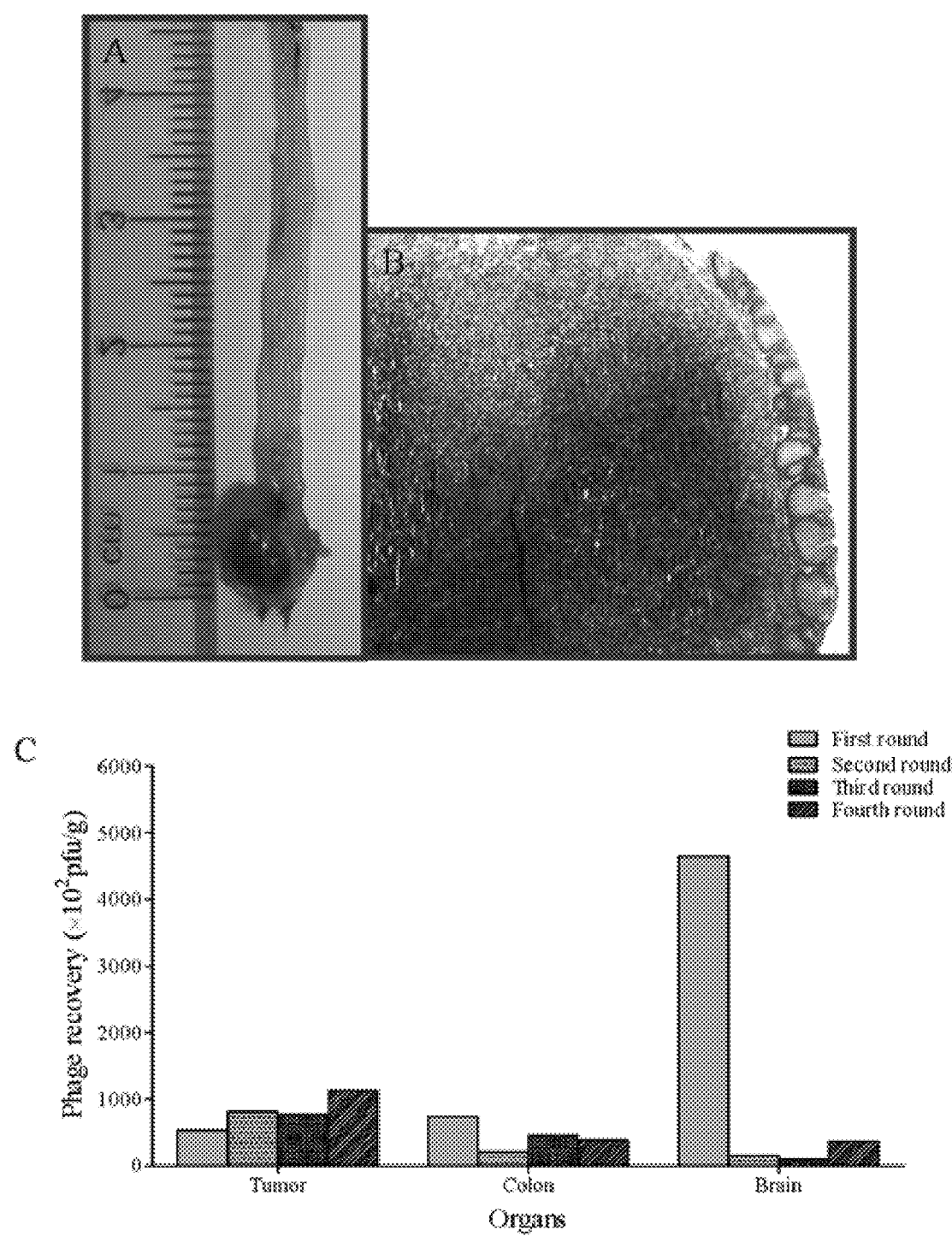
FIG. 1. describes (A) macroscopic colorectal tumors in mice; (B) microscopic confirmation of tumor development and (C) results of phage recovery for tumor specific phage using in vivo biopanning techniques.

This invention provides for 9 mer protein domain with the ability to selectively bind to vasculature growing in response to a tumor of the alimentary canal. The peptide, TCP-1, is useful in a variety of applications. It can be used as a diagnostic or as a delivery tool for concentrating chemotherapeutics to a tumor of the alimentary canal. The following description provides details on obtaining TCP-1, how to modify it for the particular use and how to formulate and administer it to patients.

1. Definitions

'Alimentary canal' refers to the mucous membrane-lined tubular pathway of the digestive system through which food enters the body, in which digestion and absorption takes place, and from which wastes are eliminated. It extends from the mouth to the anus and includes the pharynx, esophagus, stomach, small intestine, caecum and large intestine.

'Alimentary tumor vascular homing protein' refers to a protein that contains domains that selectively bind to tumor markers on tumor induced vasculature where the tumors are located on the alimentary canal of a mammal. 'Selectively binds' or "selectively homes" refers to a non-specific binding event as determined by an appropriate comparative control. Binding is selective when the binding is at least 10, 30, or 40 times greater than that of background binding in the comparative control.

Generally, selective binding or selecting homing can be demonstrated by determining if binding of a homing protein to the selected tissue is relatively specific. For TCP-1, the amount of a particular alimentary tumor vascular homing protein in cancer tissue can be compared to the amount of the homing protein that accumulates in a control organ or tissue. For example, phage expressing CTPSPFSHC (SEQ ID NO:1) will be at least two-fold, three-fold or four-fold enriched in cancer tissue (e.g. colon cancer tissue) as compared to control tissues such as normal heart tissue, normal brain tissue, normal colon tissue, normal stomach tissue (see Examples 4, 5, and 9).

'alkylating agents' refer to compounds that cause replacement of hydrogen by an alkyl group and are classified according to their nucleophilic or electrophilic character. Nucleophilic alkylating agents deliver the equivalent of an alkyl anion (carbanion). Electrophilic alkylating agents deliver the equivalent of an alkyl cation. Electrophilic, soluble alkylating agents are often cytotoxic and highly reactive. Alkylating agents inhibit cell division by reacting with DNA and are used as antineoplastic agents. Alkylating agents work by three different mechanisms to achieve disruption of DNA function and cell death. Alkyl group attachment to DNA bases results in DNA fragmentation by DNA repair enzymes. Alkylated bases prevent DNA synthesis and RNA transcription from the affected DNA. Cross-bridge formation forms covalent bonds between atoms in the DNA, within a single molecule of DNA or between two different DNA molecules. Cross-linking prevents uncoiling of the double helix for synthesis or transcription. Alkylated bases induce mispairing of the nucleotides, which, if not corrected, may lead to a permanent mutation. Some examples of alkylating agents are nitrogen mustards (bis(chloroethyl)amines; chlorambucil and cyclophosphamide); cisplatin; nitrosourea (carmustine, lomustine, and semustine); alkylsulfonates (busulfan); ethylenimines (aziridines; thiotepa); and triazines (dacarbazine).

'Antimetabolites' are chemicals that compete with, replace, inhibit or antagonize the utilization of a specific metabolite in normal metabolic functioning, acting as a structural analog of an essential nutrient. These chemotherapeutic compounds halt cell growth and cell division. Main representatives of these drugs are purine analogues (6-mercaptopurine (6 MP), azathioprine), pyrimidine analogues (5-fluorouracil (6-TG), 5-azacytidine) and antifolates (methotrexate).

'Antitumor antibiotics' refer to an anticancer drug that blocks cell growth by interfering with DNA, RNA, or ribosomal protein synthesis. Also called anticancer antibiotics and antineoplastic antibiotics. They include, e.g., doxorubicin, adriamycin, daunorubicin, epirubicin, actinomycin, bleomycin, mitomycin, mitoxantrone, plicamycin, etc.

'Anti-estrogens' refer to an estrogen antagonist or estrogen receptor modulator is a substance that blocks the activity of estrogens, the family of hormones that promote the development and maintenance of female sex characteristics. An anti-estrogen is a type of hormone antagonist that acts either by producing antagonistic effects on the target tissue or by competing with estrogens at estrogen receptors at the cellular level (tamoxifen). A "selective estrogen receptor modulator" or SERM is an "antiestrogen" agent that in some tissues acts like estrogens (agonist) but block estrogen action in other tissues (antagonist). A "selective estrogen receptor down-regulator" (SERD) or "pure" antiestrogen includes agents which block estrogen activity in all tissues.

'Bifunctional alkylating agents' refers to an alkylating agent with two reactive groups on opposite ends of the molecule, which form DNA adducts resulting in intrastrand and interstrand cross-links.

'Biologically active moiety' refers to any organic, inorganic, or living agent that is biologically active or relevant and fused to an alimentary tumor vascular homing protein. A bioactive moiety can be a protein, a polypeptide, a polysaccharide (e.g. heparin), an oligosaccharide, a mono- or disaccharide, an organic compound, an organometallic compound, or an inorganic compound. It can include a living or senescent cell, bacterium, virus, or part thereof. It can be a hormone, a growth factor, a growth factor producing virus, a growth factor inhibitor, a growth factor receptor, an anti-inflammatory agent, an antimetabolite, an integrin blocker, or a complete or partial functional insense or antisense gene. When indirectly fused to the protein the moiety can also include a man-made particle or material, which carries a biologically relevant or active material. An example is a nanoparticle comprising a core with a drug and a coating on the core. Bioactive moieties include drugs such as chemical or biological compounds that can have a therapeutic effect on a biological organism.

'Covalent bond' refers to a form of chemical bonding that is characterized by the sharing of pairs of electrons between atoms, or between atoms and other covalent bonds.

'Domain' refers to a substructure of a larger molecule. It is typically used to represent amino acid residues within a protein, or bases within a nucleic acid. A protein structural domain is a part of protein that can fold, function and exist independently of the rest of the protein chain or structure.

'Fluorophore' refers to a molecule or functional group which is capable of fluorescence. A fluorescent dye functional group in a molecule will absorb incident light of a specific wavelength and in response re-emit energy at a different specific wavelength.

Immunotherapeutic agents' refers to functional moieties that therapeutically enhance or suppress the immune system in the treatment of disease. The concept encompasses various treatment modalities including both active and passive immunization, vaccines, artificial immunosuppression or immunopotentiation, nonspecific systemic immunostimulators and adjuvants, desensitization to allergens, bone marrow transplantation, thymus implantation, treatment with cytokines or immunoconjugates, and lymphocyte deletion therapy.

'Ionic bond' refers to a bond formed by the attraction between two oppositely charged ions that involves a metal and a non-metal ion through electrostatic attraction. The metal donates one or more electrons, forming a positively charged ion or cation. These electrons are donated to the non-metal, causing it to form a negatively charged ion or anion. The atoms are thus held together by the attractive force between oppositely charged positive and negative ions to form a bond.

'Lyophilized powder' refers to a powder formed from biological substances dried by freezing and subsequent evaporation of the water in a high vacuum.

'Magnetic imaging contrast agent' refers to a composition used in magnetic resonance imaging (MRI). Image contrast agents work by creating differences in the strength of the signal recovered from different locations within the sample. This depends upon the relative density of excited nuclei (usually water protons) and on differences in relaxation times of those nuclei after the pulse. Contrast media or agents alter (shorten) these relaxation parameters. Contrast agents may be injected intravenously to enhance the appearance of blood vessels, tumors or inflammation.

'Mitotic inhibitors', also called antimitotic or antimicrotubule agents, prevent cells from undergoing mitosis, usually during the M phase of the cell cycle, by disrupting tubulin polymerization resulting in stabilization of microtubule formation. Mitotic inhibitors are a type of drug derived from natural substances such as plant alkaloids and primarily used in cancer treatment. Examples of mitotic inhibitors frequently used in the treatment of cancer include paclitaxel, docetaxel, vinblastine, vincristine, and vinorelbine.

'Nitrosourea compounds' are similar to alkylating agents, and inhibit enzymes needed for DNA repair. The nitrosoureas are lipophilic and thus are able to cross the blood-brain barrier, so they are often used in chemotherapy to treat brain tumors as well as non-Hodgkin's lymphoma, multiple myeloma, and malignant melanoma. Carmustine, lomustine, and streptozocin are examples of nitrosoureas.

'Non-steroidal aromatase inhibitors' inhibit aromatase which is the cytochrome P450 enzyme responsible for the last step of estrogen biosynthesis. This enzyme converts androgens into estrogens by aromatization. Nonsteroidal aromatase inhibitors (NSAIs) are competitive inhibitors of aromatase. In post-menopausal women, most of the body's estrogen is produced in the adrenal gland from the conversion of androgens. Because some breast cancers respond to estrogen, lowering the estrogen level using aromatase inhibitors in postmenopausal patients failing antiestrogen therapy alone or multiple hormonal therapies has been proven to be effective in hormone-dependent breast cancer treatment. Some of the aromatase inhibitors in use include arimidex (anastrozole) and femara (letrozole).

'Pharmaceutically acceptable composition' refers to compositions comprising an auxiliary agent in addition to the therapeutic agent. They are non-toxic reagents acceptable for medical use and selected from the group consisting of a pharmaceutically acceptable carrier, diluent, salt, buffer, or excipient, such as sterile saline or other medium, water, gelatin, oil, etc. The pharmaceutical compositions of the invention may be a solution or a lyophilized product.

'Radiopaque dye' also known as radiopaque contrast media or radiographic contrast media, do not allow the passage of X rays or other radiation. They are used in radiology to enhance the X-ray pictures to outline certain organs during X-ray examination or to outline the interior of hollow organs, such as heart chambers, blood vessels, respiratory passages, and the biliary tract. Radiopaque dye (contrast agent) is given, usually by injection, by mouth, or into the rectum.

'Radiolabel' refers to a compound used to tracking the passage of a sample of substance through a system, where a radioactive isotope used as a tracer. A compound is "labelled" by including or introducing radionuclides in its chemical composition. When these decay, their presence can be determined by detecting the radiation emitted. Radioisotopic labelling is a special case of isotopic labeling, whereby the substance is "labeled" by including unusual isotopes in its chemical composition. The radiolabel is chemotherapeutic when the decay particles are in sufficient amount to inhibit cell growth and reduce the tumor load on the patient.

'Reduce the tumor load' refers to an inhibition of the growth of tumors or a reduction of tumor volume in a patient hosting a tumor. Reduction can be measured by assaying tumor biomarkers or by visual inspection of the tumor volume.

'Selectively binds' refers to a non-specific binding event as determined by an appropriate comparative control. Binding is selective when the binding is at least 10, 30, or 40 times greater than that of background binding in the comparative control.

'Tumor induced vasculature' or tumor neovasculature is characteristic of tumor growth and the formation of metastases. Remodeling of the vascular bed during tumor angiogenesis exhibits both coiling vessels and an increase of the vascular net. Vascular maturation and stabilization is a secondary process, which involves the recruitment of vascular smooth muscle cells and pericytes. The existence of a window of plasticity in the newly formed blood vessels thus provides promising potential therapeutic targets. This plasticity window provides the possibility for selective obliteration of immature tumor neovasculature. The therapeutic applicability of neovascular obliteration by antiangiogenic therapy depends on the fact that mature blood vessels are not susceptible to such damage.

'Topoisomerase I inhibitors' are a type of DNA topoisomerase. DNA topoisomerases are a class of enzymes involved in the regulation of DNA supercoiling. Type I topoisomerases change the degree of supercoiling of DNA by causing single-strand breaks and re-ligation. These activities are especially crucial during DNA transcription and replication, when the DNA helix must be unwound to allow proper function of large enzymatic machinery, and topoisomerases have indeed been shown to maintain both transcription and replication. Topoisomerase I inhibitors include irinotecan, topotecan, camptothecin and lamellarine D. Camptothecins are effective against previously resistant tumors and are the only class of topoisomerase I (Top1) inhibitors approved for cancer treatment.

2. Obtaining TCP-1

The TCP-1 peptides and derivatives may be synthesized de novo using conventional solid phase synthesis methods. Our peptides were prepared by commercial services. In such methods, the peptide chain is prepared by a series of coupling reactions in which the constituent amino acids are added to the growing peptide chain in the desired sequence. These general methods include exclusive solid phase synthesis, partial solid phase synthesis methods, fragment condensation, classical solution synthesis. These methods are preferably utilized when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures and purification are well known in the art and further described in Solid-Phase Synthesis: A Practical Guide by Steven A Kates, Fernando Albericio (Editor), CRC Press 2000-04 and in Peptide Synthesis Protocols, Methods in Molecular Biology, Volume 35, by Michael W. Pennington and Ben M. Dunn Humana Press 1994. A preferred peptide synthesis method follows conventional Merrifield solid phase procedures well known to those skilled in the art. Crude peptide preparations resulting from solid phase syntheses may be purified by methods well known in the art, such as preparative HPLC and the composition of which can be confirmed via amino acid sequencing.

Alternatively TCP-1 can be produced using recombinant techniques as described in basic texts such as Current protocols in molecular biology, by Frederick M Ausubel et al; John Wiley & Sons, 2007-updated; and Molecular Cloning: A Laboratory Manual, by Joseph Sambrook and David W Russell; Cold Spring Harbor Laboratory Press, 2001. Cell free synthesis methods can also be used to produce TCP-1 as described in Cell-free Protein Synthesis: Methods and Protocols, by James R Swartz, Weinheim:Wiley-VCH, 2008.

Oligonucleotides encoding TCP-1 protein can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

To obtain high level expression of a cloned gene, such as those genes encoding TCP-1 in prokaryotes and eukaryotes, one typically subclones the gene into an expression vector that contains a strong promoter to direct transcription, a transcription/translation terminator, and a ribosome binding site for translational initiation. Suitable bacterial promoters are well known in the art and described in the text books identified above. Bacterial and eukaryotic expression systems for expressing TCP-1 protein are readily available as kits from a variety of commercial sources. Eukaryotic expression systems would include mammalian cells, yeast, and insect cells.

After the expression vector is introduced into the cells, the transfected cells are cultured under conditions favoring expression of TCP-1, which is recovered from the culture using standard techniques identified below.

TCP-1 may be purified to substantial purity by standard techniques, including selective precipitation with such substances as ammonium sulfate; column chromatography, immunopurification methods, and others (see, e.g., Protein Purification Techniques: A Practical Approach (Practical Approach Series) by Simon Roe: Oxford Univ. Press, 2006; and Protein purification principles and practice by Robert K Scopes Springer 1987.

3. Modifications to TCP-1

Modifications to TCP-1 fall into two categories. Modifications that improve its homing ability and modifications that provide functional activity apart from the homing ability. The functional activity can be further divided in to activity that permits detection and activity that is biological.

To improve tumor vasculature homing ability, TCP-1 may be incorporated into a variety of scaffolds. These include both peptide and non-peptide scaffolds. The simplest modification is the addition of amino acids fused to the TCP-1 termini to act as linking groups or spacers. In the examples below, a two-glycine linker is described. The fusion of additional amino acids to TCP-1 domains can be simple or complex and may involve using the amino acids as a spacer between TCP-1 domains or as a linker at the end of a single TCP-1 domain.

Peptide scaffolds useful for presenting TCP-1 are well known and include carrier peptides and antibody mimics. One or more copies of the TCP-1 domain can be inserted into the binding regions of scaffolds to enhance activity. Peptide scaffolds would ideally have little or no immunogenicity and would include proteins such as human albumin, peptide-IgG chimeras (Epitope-Specific Tolerance Induction with an Engineered Immunoglobulin Elias T. Zambidis and David W. Scott, *PNAS, Vol.* 93, No. 10 (May 14, 1996), pp. 5019-5024) collagen or ferritin (Carter, et al. U.S. Pat. No. 7,097,841). Antibody mimics include Ku et al. (Proc. Natl. Acad. Sci. U.S.A. 92(14):6552-6556 (1995)) disclosing an alternative to antibodies based on cytochrome b562; and, Lipovsek et al. (U.S. Pat. Nos. 6,818,418 and 7,115,396) disclosing an antibody mimic featuring a fibronectin or fibronectin-like protein scaffold and at least one variable loop. Further peptide scaffolds would include those described by Beste et al. (*Proc. Natl. Acad. Sci. U.S.A.* 96(5):1898-1903 (1999)) based on a lipocalin scaffold (Anticalin®). Hamilton et al. (U.S. Pat. No. 5,770,380) discloses a synthetic antibody mimic using the rigid, non-peptide organic scaffold of calixarene, attached with multiple variable peptide loops used as binding sites. Murali et al. (*Cell Mol Biol* 49(2):209-216 (2003)) discusses a methodology for reducing antibodies into smaller peptidomimetics, they term "antibody like binding peptidomimetics" (ABiP) which are useful as scaffolds for presenting domains of TCP-1.

Nonproteinaceous polymers to which TCP-1 may be introduced include, but are not limited to, polyalkylethers as exemplified by polyethylene glycol and polypropylene glycol, polylactic acid, polyglycolic acid, polyoxyalkene, polyvinylalcohol, polyvinylpyrrolidone, cellulose and cellulose derivatives, dextran and dextran derivatives. In addition agarose and hyaluronic acid may be used. Generally, such hydrophilic polymers have an average molecular weight ranging from about 500 to about 100,000 daltons, including from about 2,000 to about 40,000 daltons and, from about 5,000 to about 20,000 daltons. The hydrophilic polymers also can have an average molecular weights of about 5,000 daltons, 10,000 daltons and 20,000 daltons.

Polymeric moieties may be covalently bound through amino acid residues fused to TCP-1 via a reactive group, such as a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

To facilitate the above modifications, TCP-1 or its scaffold may be derivatized with additional functional groups and/or linked to other molecules to facilitate their attachment to the scaffold or to functional moieties. Commercially available linkers include homo-bifunctional and heterobifunctional linkers. Among the homobifunctional coupling agents, there may be mentioned DITC (1,4-phenylene diisothiocyanate), DSS (disuccinimidyl suberate) or the like. Among the heterobifunctional coupling agents, there may be mentioned SMCC (succinimidyl-4-(N-maleimidomethyl)cyclohexane-1-carboxylate), or SMPB (succinimidyl-4-(p-maleimidophenyl) butyrate).

TCP-1 or its scaffold may be complexed covalently or non-covalently to other pharmaceuticals, bioactive agents, or other functional moieties as described herein. As with the fusion proteins or scaffolds such derivatizations must be accomplished so as to not significantly interfere with the tumor vascular homing properties of TCP-1. Functional groups which may be attached to the peptides may include, but not be limited to, amines, alcohols, or ethers.

A peptide of the invention and a carrier molecule may be conjugated directly or indirectly via a linker moiety. Direct conjugation may occur through any convenient functional group such as a hydroxy, carboxy or amino group. In one aspect, conjugation is via a covalent bond. In one aspect, the carrier molecule may be attached to either end of a TCP-1 peptide of the invention, e.g., a carrier molecule may be attached to the terminal amino acid residue or to the terminal carboxy amino acid residue of the TCP-1 or its protein scaffold.

Amino terminus modifications include, but are not limited to, alkylating, acetylating and adding a carbobenzoyl group, forming a succinimide group (see, e.g., Murray et al. (1995) Burger's Medicinal Chemistry and Drug Discovery, 5th ed., Vol. 1, Manfred E. Wolf, ed., John Wiley and Sons, Inc.). C-terminal modifications include mimetics wherein the C-terminal carboxyl group is replaced by an ester, an amide or modifications to form a cyclic peptide beyond the C-C loop of TCP-1.

Methods for derivatizing peptide compounds or for coupling peptides to such polymers have been described (see, e.g., Zallipsky (1995) Bioconjugate Chem., 6:150-165; Monfardini et al. (1995) Bioconjugate Chem., 6:62-69; U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 and WO95/34326, all of which are incorporated by reference in their entirety herein).

After derivitization and attachment of scaffold and/or carriers, the TCP-1 polymer may be of any molecular weight, and may be branched or unbranched. The polymers conjugated to TCP-1 should be attached with consideration of effects on functional or antigenic domains of the TCP-1 domains. The number of copies of TCP-1 per protein or scaffold molecule is not critical and may be as low as 2-5 copies or as high as 50 to 100 or more copies.

The TCP-1 domains may also be presented as multimeric polypeptides. In such a configuration the TCP-1 domains are combined into a protein having quaternary structure. For example, TCP-1 containing polypeptides can be fused to via leucine zipper or isoleucine zipper.

Having described the various configurations that TCP-1 may be modified for targeting tumor vasculature in the alimentary canal, there are a variety of functional moieties to which TCP-1 domains may be joined. These include detectable labels. The particular label or detectable group used in the assay is not a critical aspect of the invention, as long as it does not significantly interfere with the specific binding of the TCP-1 domains to their target vasculature. The detectable group can be any material having a detectable physical or chemical property. Such detectable labels have been well-developed in the field of diagnostics and, in general, most any label useful in such methods can be applied to the present invention. Thus, a label is any composition detectable by spectroscopic, photochemical, biochemical, immunochemical, electrical, optical or chemical means. Useful labels in the present invention include imaging contrast agents, radiopaque dyes, magnetic beads (e.g., DYNABEADS™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

Means of detecting labels are well known to those of skill in the art. Thus, for example, means for detection include medical devices such a MRI or CAT scanners when detection is done inside a patient. When externally detected, a scintillation counter or photographic film as in autoradiography may be used. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label.

In addition to detectable labels, functional moieties include biologically active moieties especially chemotherapeutic agents that provide superior activity when targeted to the tumor by TCP-1 domains. Examples of drugs which can be included in such TCP-1 compositions include, but are not limited to, toxins, such as enzymatically active toxins of bacterial, fungal, plant, or animal origin, or fragments thereof [e.g., diphtheria toxin, exotoxin A chain of *Pseudomonas aeruginosa*, ricin A chain, abrin A chain, modeccin A chain, .alpha.-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes], radioisotopes (e.g., $^{125}I$, $^{131}I$, $^{90}Y$, $^{212}Bi$ and $^{198}Re$) and chemotherapeutic agents (e.g., alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Specific examples include, Adriamycin, Doxorubicin, 5-Fluorouracil, Cytosine arabinoside (i.e., Ara-C), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see U.S. Pat. No. 4,675,187), Melphalan, and other related nitrogen mustards. Also included are hormonal agents that act to regulate or inhibit hormone action on tumors, such as tamoxifen and onapristone.

For in vivo applications, the TCP-1 peptides or peptide-active agent conjugates of the present invention may comprise a pharmaceutically acceptable salt. Suitable acids are capable of forming such salts with the compounds of the present invention. These would include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

4. Formulation and Administration

A pharmaceutical composition of the above described TCP-1 domain containing compositions is formulated with pharmaceutically acceptable carriers compatible according to the intended route of administration. Examples of routes of administration include parenteral, e.g., intravenous, intradermal, subcutaneous, oral and rectal administration. Pharmaceutically acceptable carriers include physiologically tolerable or acceptable diluents, excipients, solvents or adjuvants. The compositions are preferably sterile and nonpyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum metahydroxide, bentonite, kaolin, agar-agar and tragacanth, or mixtures of these substances, and the like.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In all cases, injectable compositions must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The compounds described herein can also be prepared in the form of suppositories (e.g., with conventional suppository bases such as cocoa butter and other glycerides) or retention enemas for rectal delivery.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Generally, the amount of TCP-1 containing peptide administered depends upon the intended use of the peptide. If detection is the objective, one administers sufficient material to detect its concentration at the tumor sites. For therapeutic uses, the intent is to reduce the patient's tumor load and the precise amount of drug depends on the therapeutic agents being delivered. Those skilled in the art may derive appropriate dosages and schedules of administration to suit the specific circumstances and needs of the patient. Typically, dosages of TCP-1 peptide are between about 0.001 mg/kg and about 100 mg/kg body weight. In some embodiments dosages are between about 0.01 mg/kg and about 60 mg/kg body weight. In other embodiments, dosages are between about 0.05 mg/kg and about 5 mg/kg body weight.

In general, the schedule or timing of administration of TCP-1 peptides of the invention will be according to the accepted practice for the procedure being performed. For diagnostics a single administration is generally sufficient per diagnostic procedure. For reduction of tumor load, multiple administrations are anticipated. Tumor load reduction can be visually measured using TCP-1 diagnostic composition as described above or by detection of tumor markers of the alimentary canal. Such markers are well known (see for example—U.S. Pat. Appl. Nos. 20090155820 and 20090075312 disclosing ACS, osteopontin and carcinoembryonic antigen as CRC markers; U.S. Pat. Appl. No. 20090170100 and 20070054282 disclosing markers for gastric cancer; and Jin Z et al. Hypermethylation of the AKAP12 promoter is a biomarker of Barrett's-associated esophageal neoplastic progression. *Cancer Epidemiol Biomarkers Prev.* 2008 January; 17(1):111-117.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

TCP-1 was identified using in vivo panning using phage display. Once identified TCP-1 was demonstrated to be specific to the vasculature supporting both colon and gastric cancers. In addition, TCP-1 was demonstrated to be selective for the tumor vasculature of the alimentary canal. The following examples describe our work.

Example 1

General Methods

Tumor cell line and cell culture: To identify and demonstrate the binding specificity of TCP-1 to the vasculature of tumors of the alimentary canal, we used the murine colorectal cancer cell line colon 26, human colon adenocarcinoma cell HCT116 and HT-29. The colon 26 cell line was originally obtained from Cell Resource Center for Biomedical Research, Institute of Development, Aging and Cancer, Tohoku University (Sendai, Japan). The human colon adenocarcinoma cell HCT116 and HT-29 was purchased from the American Type Culture Collection. The two cell lines were cultured at 37° C. in a humidified atmosphere containing 5% $CO_2$, in RPMI-1640 medium (Invitrogen) supplemented with 2 g/L sodium bicarbonate, 100 units/ml penicillin (ICN Biomedicals, Costa Mesa, Calif.), 100 mg/ml streptomycin (ICN Biomedicals, Aurora, Ohio), pH 7.4 and 10% fetal bovine serum (FBS, Invitrogen).

Phage Display Library: TCP-1 was isolated from the Ph.D.™-C7C Phage Display Peptide Library from New England Biolabs. This phage library is based on a combinatorial library of random heptapeptides fused to a minor coat protein (pIII) of M13 phage (1-6). The randomized sequence is flanked by a pair of cysteine residues. Under nonreducing conditions the cysteines will spontaneously form a disulfide cross-link, resulting in phage display of cyclized peptides, Antibody: To detect the TCP-1 specific phage, rabbit anti-fd bacteriophage antibody was purchased from Sigma. This antibody binds specifically to phage coat proteins of fd phage or M13 phage. Rat anti-mouse CD31 monoclonal antibody was purchased from BD Pharmingen. Mouse anti-human CD31 monoclonal antibody was ordered from DAKO. Cleaved caspase3 antibody was from Cell Signaling Technology. Alexa Fluor 568 goat anti-rat IgG (H+L), Alexa Fluor 568 goat anti-mouse IgG (H+L) and Alexa Fluor 488 goat anti-rabbit IgG were purchased from Invitrogen.

Peptide synthesis of TCP-1: Having identified TCP-1 from the in vivo bio-panning, we had synthetic peptides synthesized for further experiments. The synthetic peptides CTPSPFSHC (SEQ ID NO:1), CTPSPFSHC-GG-$_D$(KLAKLAK)$_2$ and $_D$(KLAKLAK)$_2$ were obtained commercially (AnaSpec) to our specifications. For in vivo peptide homing validation, FITC-conjugated CTPSPFSHC (SEQ ID NO:2) and FITC-conjugated CVQTAQLLC (SEQ ID NO:3) (negative control) were also obtained.

Orthotopic colorectal cancer model: Male BALB/c mice aged 9 weeks were used in the studies that led to the discovery of TCP-1. The mice were maintained at Chinese University of Hong Kong Animal Facility. All animals were housed in plastic cages (four or five mice/cage) with free access to drinking water and a pelleted basal diet, under controlled conditions of humidity (50±10%), light (12/12 h light/dark cycle) and temperature (23±2° C.).

The model was performed as previously published with some modifications. (See Takahashi T, Morotomi M, and Nomoto K (2004). A novel mouse model of rectal cancer established by orthotopic implantation of colon cancer cells. *Cancer Sci* 95, 514-519). Briefly, all mice were given the tap water containing 3% dextran sulfate sodium (DSS) for 8 days to induce colitis. Mice were fasted for 18 h (DSS) after colitis induction, and then anesthetized with sodium pentobarbital. Colon 26 cells ($3 \times 10^6$ cells/40 µl/mouse) were infused intrarectally with a micropipette inserted 2 cm into the anus of the mice. The anus was compressed with a noncrushing microclamp immediately after instillation of tumor cells for 30 min to prevent leakage. Successful models were used for in vivo selection at 2 weeks after implantation of tumor cells.

In addition, for subcutaneous cancer model induced by colon 26, male normal BALB/c mice at 9 weeks of age were s.c. injected with $2 \times 10^6$ colon 26 cells in 150 µl PBS. Tumors were allowed to grow for 10 days and mice were used to perform phage homing ability assay. For subcutaneous model induced by HT-29 and HCT116, male BALB/c nude mice at the age of 6-8 weeks old were s.c. injected with $3 \times 10^6$ cells/150 µl PBS. Tumors were allowed to grow for 2 weeks and mice were used to perform phage homing ability assay.

In vivo phage display biopanning: The biopanning procedure that identified TCP-1 was achieved as previously described. (See Trepel M, Pasqualini R, and Arap W (2008). Chapter 4. Screening phage-display Peptide libraries for vascular targeted peptides. *Methods Enzymol* 445, 83-106 and Christianson D R, Ozawa M G, Pasqualini R, and Arap W (2007). Techniques to decipher molecular diversity by phage display. *Methods Mol Biol* 357, 385-406).

Briefly, mice bearing colon tumors were anesthetized and i.v. injected with a C7C phage library (New England Biolabs) in 300 µl TBS containing $5 \times 10^{10}$ pfu (plaque forming unit) phage. After 8 minutes, the mice were perfused through the heart with DMEM containing 1% BSA. For the first round of selection, 2 ml perfusion solution was used to obtain enough peptide sequences. The tumor and control organs were dissected from each mouse and the phage was rescued and titered. From the second round, the perfusion solution was increased to 5 ml to remove the unspecific binding clones. After fourth round biopanning, 80 phage clones were picked and suspended in 20 µl PBS.

PCR was used to amplify the inserted fragments, and, finally, sequenced the PCR products. The following primer pairs were utilized for PCR: 5'-AGC AAG CTG ATA AAC CGA TAC AAT-3' (SEQ ID NO:4) (forward) and 5'-TAC CGT AAC ACT GAG TTT CGT CAC-3' (SEQ ID NO:5) (reverse). 66 clones had their displayed peptides obtained. Four peptides appeared more than once among the 66 phage clones analyzed. CTPSPFSHC-phage (TCP-1 phage) with the most frequent appearance was chosen for further examination.

In vivo phage targeting assay: An in vivo phage targeting assay was used to demonstrate that the homing properties of TCP-1 were due to TCP-1 and not some other aspect of the phage. The assay was as described in Zhang L, Giraudo E, Hoffman J A, Hanahan D, and Ruoslahti E (2006). Lymphatic zip codes in premalignant lesions and tumors. *Cancer Res* 66, 5696-5706. Briefly, mice bearing tumors were anesthetized and i.v. injected with $1 \times 10^9$ pfu CTPSPFSHC-phage or control phage. After 8 minutes, mice were perfused through the heart with DMEM containing 1% BSA. The tumor and control organs were removed from each mouse and the phage was rescued and titered. For histology analysis, the mice were perfused with 4% paraformaldehyde 1 hour after the injection of phage. Tissues were removed, soaked in 28% sucrose in PBS overnight, and embedded in Tissue-Tek OCT (Tissue-Tek, SAKURA). 10 µm sections were prepared for phage immunostaining as described below.

Immunohistology: Frozen tissue sections were cut, air-dried on slides, rinsed twice for 5 min with PBS and then blocked with 10% normal goat serum in PBS for 1 h. Tissue sections were incubated for 1 h in 10% normal goat serum containing monoclonal rat anti-CD13 (1:100) and rabbit anti-fd bacteriophage antibody (1:200). Slides were then rinsed three times with PBS for 5 min each and incubated for 1 h with a 0.22 µm-filtered secondary antibody solution (10% normal goat serum) containing Alexa Fluor 488 goat anti-rabbit IgG (1:1000) and Alexa Fluor 568 goat anti-rat IgG (1:500). Slides were rinsed three times for 5 min each with PBS, and staining of nuclei were performed with DAPI for 5 min. Finally, Slides were rinsed three times for 5 min each with PBS, mounted with nail polish and observed under fluorescent microscopy.

Imaging of tissue was done under a blue light, by using the imaging system of KODAK Image Station 2000MM.

Example 2

Isolating Phage that Home to the Orthotopic Colorectal Cancer Tissue

To isolate phages specific for colorectal cancer, we used the above described orthotopic colorectal cancer mouse model to perform the in vivo phage library selection. Orthotopic tumor formed at 2 weeks after BALB/C mice were given 3% DSS tap water and implanted mouse colon cancer cell colon 26 from anus. Macroscopically, colorectal tumors were observed in the distal colon and rectum of mice (FIG. 1A). Tumor formation was confirmed by histological analysis (FIG. 1B). A tumor in nodular form growing at the intraluminal aspect of the colorectal mucosa was clearly seen at 2 weeks after implantation of colon 26 cells.

In order to enrich phage that bind to cancer tissue but not to control organs, four rounds of in vivo selection from a 7-mer cyclic peptide library on the model yielded a pool with 3-fold increase over the first round (FIG. 1C). There was no enrichment in the several control organs tested: brain, heart and colon (FIG. 1C). We performed DNA sequence analysis of 80 phage clones isolated in the fourth in vivo round of phage pool. 66 clones had their displayed peptides obtained. Four peptides appeared more than once among the 66 phage clones analyzed. CTPSPFSHC-phage (termed TCP-1 phage) with the most frequent appearance was chosen for further examination.

Example 3

Validation of CTPSPFSHC-Phage Homing To Colorectal Cancer Tissue

Figure 2:
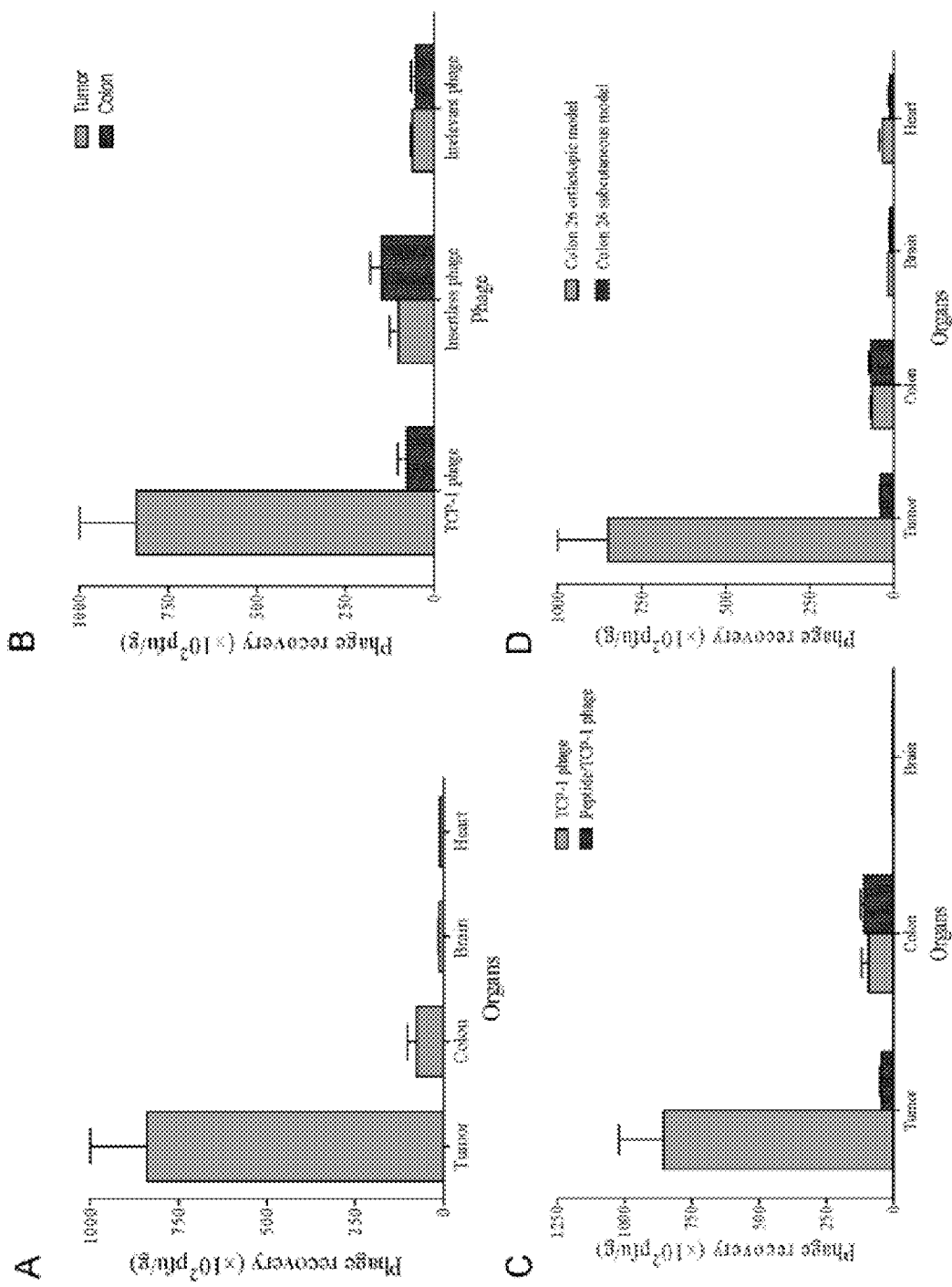
FIG. 2. describes validation of colorectal tumor specificity of TCP-1 (A) TCP-1 phage (B) TCP-1 versus control phage; (C) TCP-1 phage versus TCP-1 peptide; (D) TCP-1 phage comparing colon 26 colorectal tumors and colon 26 subcutaneous tumors (sc); (E) TCP-1 phage comparing binding specificity between colon 26 orthotopic model versus HT-29 subcutaneous model; and, (F) TCP-1 phage comparing binding specificity between colon 26 orthotopic model versus HCT-116 subcutaneous model.
Figure 2:
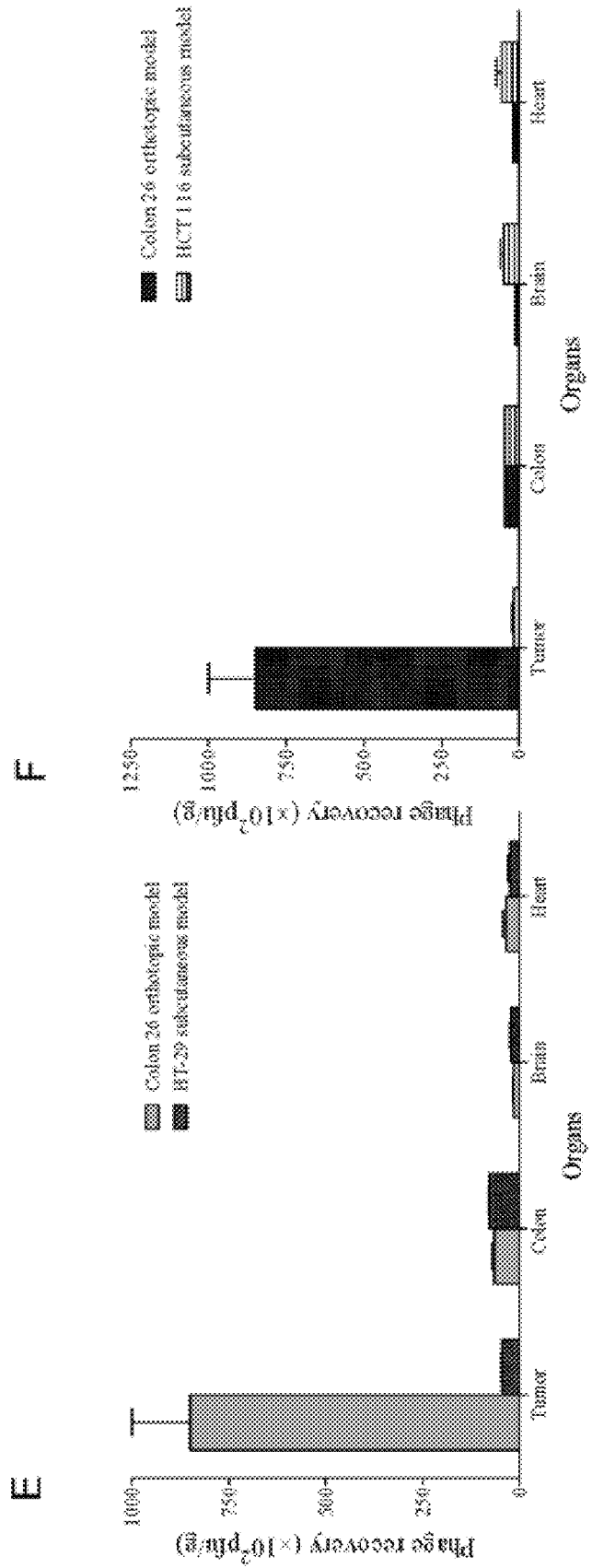

To analyze the specificity of tumor-homing ability for CTPSPFSHC-phage under in vivo conditions, we intravenously injected purified CTPSPFSHC-phage or control phage (insertless phage and irrelevant phage) into colon-tumor-bearing mice. Both tumor tissue and normal control organs were collected and titered for phage accumulation. Phage displaying peptide CTPSPFSHC (SEQ ID NO:1) was enriched from 11 to 94-fold higher in tumor tissue than in control organs including colon, brain and heart (FIG. 2A). Two control phages were found to be less selective for tumor tissue and normal colon organ (FIG. 2B).

To investigate whether the homing ability of CTPSPFSHC-phage is due to the displayed peptide sequence, we co-injected the CTPSPFSHC-phage with chemically synthetic CTPSPFSHC (SEQ ID NO:1) (300 µg) into the tumor-bearing mice. Phage number recovered from the tumor tissue was reduced by 95%, but control organs such as brain and colon were not much affected (FIG. 2C).

Interestingly, we found that the CTPSPFSHC-phage homed less efficiently to s.c. tumor of colon 26 in nude mice than to orthotopic tumor in normal mice of the same cell line (FIG. 2D). Meanwhile, CTPSPFSHC-phage did not bind to s.c. xenografts induced by human colon cancer cell line HT-29 or HCT-116 (FIG. 2E-F). Thus, CTPSPFSHC-phage seems to specifically recognize orthotopic colorectal cancer tissue, which implies the importance and uniqueness of colonic microenvironment. This simulates the conditions of colorectal cancer in humans.

Example 4

Biodistribution of the CTPSPFSHC-Phage

Figure 3A:
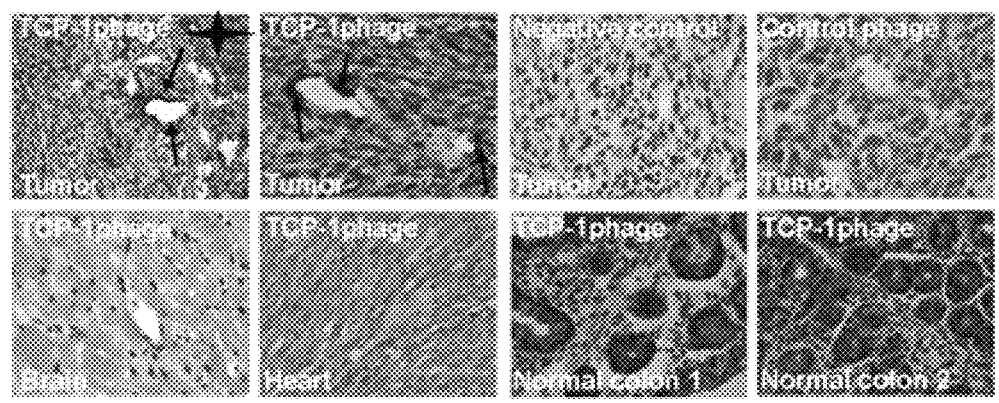
FIG. 3. describes biodistribution of TCP-1 phage. (A) Comparing binding of insertless phage (control) and TCP-1 phage in various mouse tissue; and, (B) fluorograms of TCP-1 phage and control phage using various stains having distinct fluorophores.
Figure 3B:
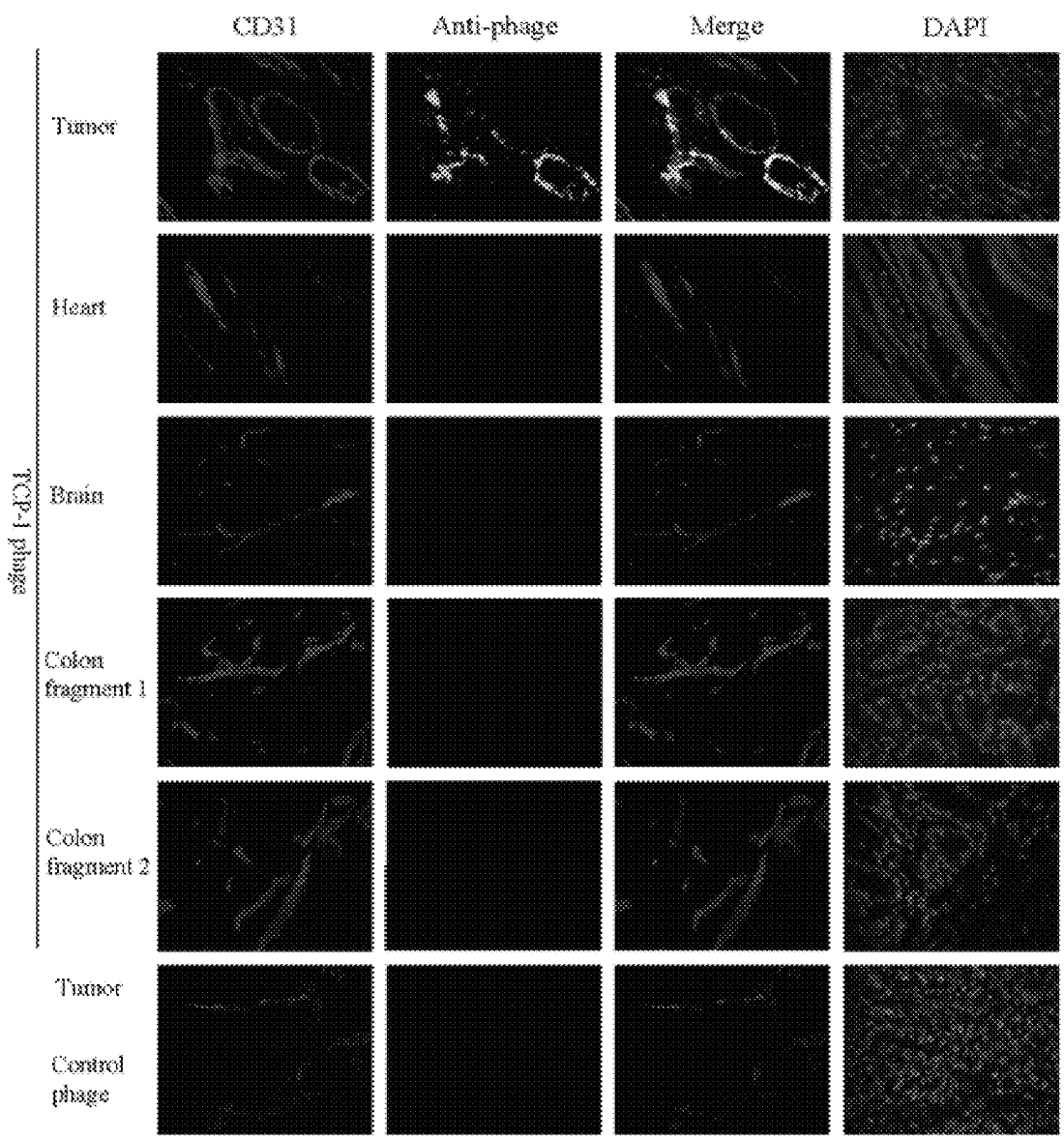

We examined the bio-distribution of CTPSPFSHC-phage using immuno-histochemistry (DAB development) with the Fd anti-phage antibody after intravenous injection. Tumor tissue and control organs were removed and prepared frozen sections. The CTPSPFSHC-phage was found to localize in tumor tissues, but not control organs such as heart, brain and normal colon tissues, etc. Insertless phage was not detectable in the tumor tissues (FIG. 3A). Subsequently, double label immunofluorescent staining (described above in Example 1) was used to visualize the colocalization of phage with phage antibody and an anti-CD31 antibody that marks the endothelial cells of the vasculature. CTPSPFSHC-phage colocalised with CD-31 positive endothelial cells in tumor tissues but not with the vessels in control organs. Insertless phage did not react with the vasculature of tumor tissues. By overlaying images of the two labels, we determined that the phage colocalised with the CD31 indicating the selectivity of TCP-1 for tumor induced vasculature.

Example 5

Bio-Distribution of the FITC-Conjugated CTPSPFSHC (SEQ ID NO:2)

To further confirm whether the selective phage homing was due to the CTPSPFSHC (SEQ ID NO:1) peptide (TCP-1), chemically synthetic FITC-conjugated TCP-1 or control peptide was intravenously injected into tumor-bearing mice to study the location of the peptide. Biodistribution of fluorescein-conjugated peptides was examined after i.v. injection of the peptide (300 nmol in 300 µl PBS) into the tail vein of a tumor-bearing mouse. The peptide was allowed to circulate for 1 hour.

Figure 4A:
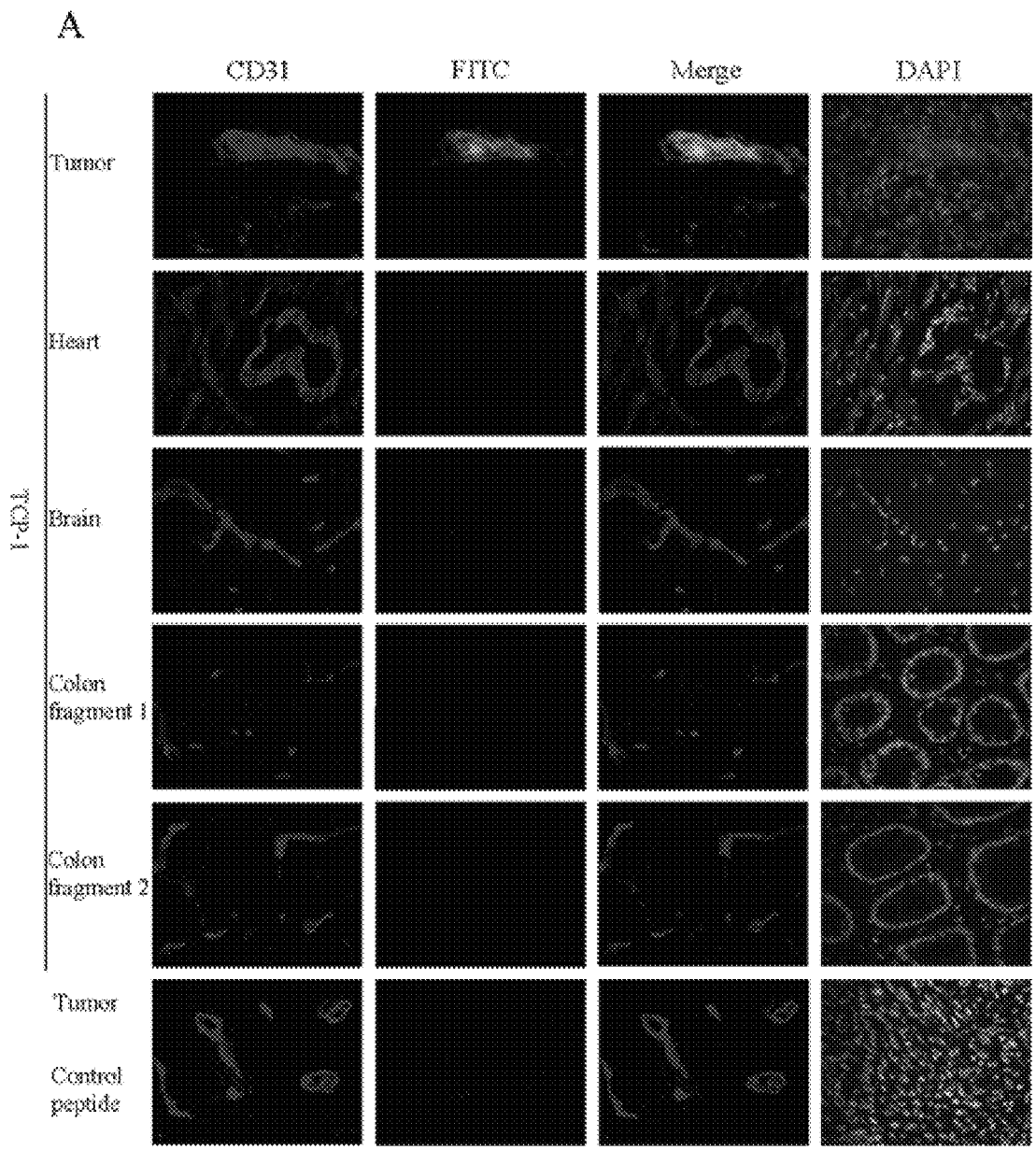
FIG. 4. describes biodistribution of TCP-1 peptide in various tissues.

Tumor and control tissues were collected and frozen sections prepared as described above in Example 1. Blood vessels were stained by CD31 antibody (secondary antibody conjugated Alexa-568). The FITC-labeled TCP-1 colocalised with CD31 in the tumor tissues (FIG. 4A). But it was not detectable in control organs (FIG. 4A). FITC-labeled control peptide was not found in the tumor tissues (FIG. 4A). Taken together with the immunolocalization analyses of TCP-1 phage homing, the peptide localization data confirmed that TCP-1 peptide homed specifically to blood vessels in tumor tissues but not to the vasculature of control organs.

Example 6

Imaging Detection of the Tumor Tissues by the TCP-1 Peptide

To determine whether FITC-labeled TCP-1 accumulated into the tumor tissues can be visualized at the organ level, tumor-bearing mice were injected intravenously with FITC-labeled TCP-1, control peptide or PBS alone. More specifically, tumor-bearing mice were i.v. injected with 500 nmol fluorescein-conjugated peptide (in 500 µl PBS). The peptide was allowed to circulate for 20 hour. The mice were killed, and various tissues were excised and examined for fluorescence. Organ imaging was done under a blue light, by using the imaging system of KODAK Image Station 2000MM. Our study showed that tumor size as small as 2 mm could be detected under the present experimental conditions.

Figure 5:
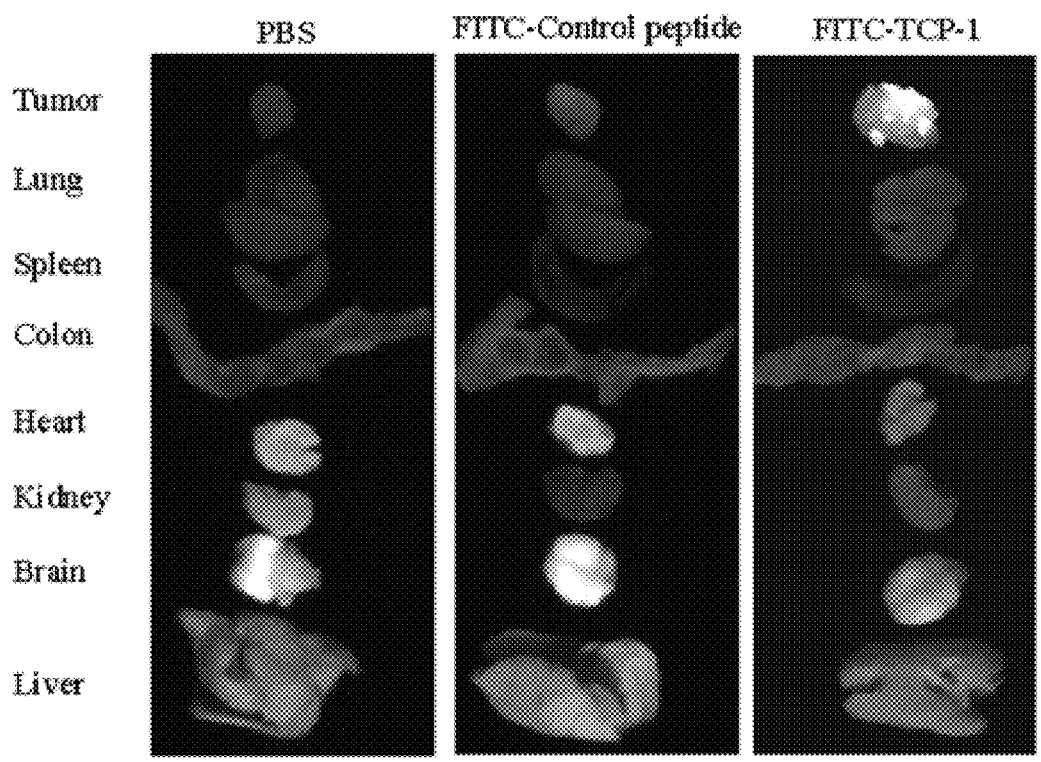
FIG. 5. describes organ level detection of TCP-1 peptide. (A) describes TCP-1 selective binding in colorectal tumors versus other organs; and, (B) describes TCP-1 selective binding in colorectal tumors of varying size; (C) TCP-1 peptide fluorescence remained in the vasculature of tumor tissue but not in the control organs. FITC-labeled control peptide was not detectable in the tumor tissues.
Figure 5:
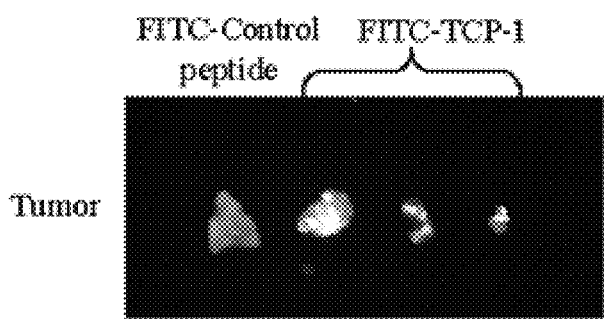
Figure 5:
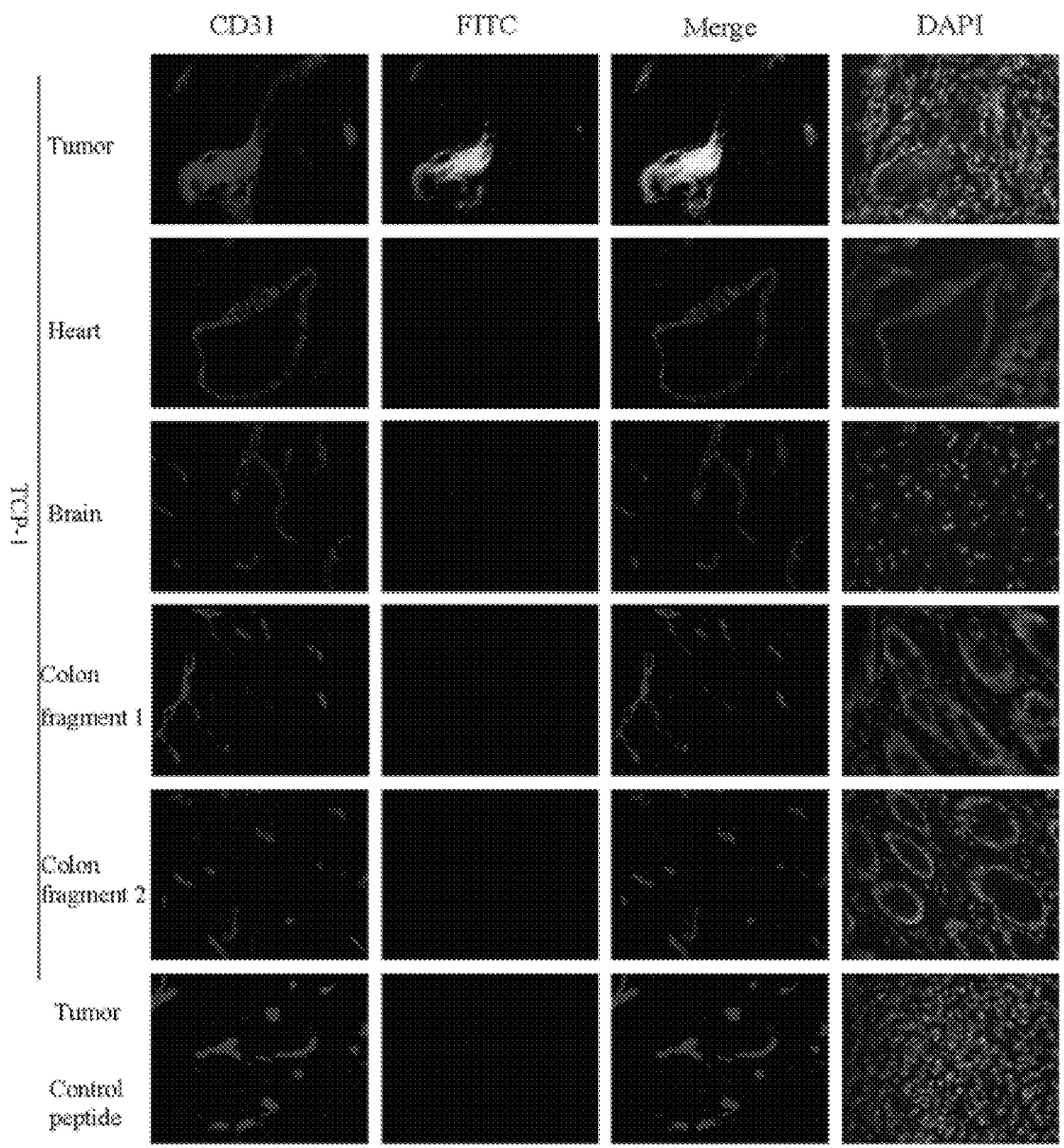

Examination of whole tissues from these mice under blue light 20 h after injection disclosed strong fluorescent signal in tumors from the mice injected with TCP-1 (FIG. 5A), whereas no fluorescent signal was detectable in the tumors from the control peptide or PBS-injected mice (FIG. 5A). We also detected no specific fluorescent signal in other control tissues with either peptide or PBS alone (FIG. 5A). Further, FITC-labeled TCP-1 could specifically accumulate in the tumor tissues with various volumes (diameter 2 mm, 6 mm, 8 mm tested) (FIG. 5B).

Histological analysis for these tissues determined that TCP-1 peptide fluorescence remained in the vasculature of tumor tissue but not in the control organs. FITC-labeled control peptide was not detectable in the tumor tissues (FIG. 5C).

Example 7

TCP-1 Selective Binding to Tissue Sections from Human Cancer

To establish the ability of TCP-1 to selectively bind to the vasculature of human tumors, human biopsy samples were studied. They were double stained and images photographically overlayed to determine tissue specificity. More specifically, multiple human biopsy samples containing both colon adenocarcinoma and normal colonic tissue were snap frozen, embedded in OCT, cut into 5 µm sections, and then arrayed on slides. The slides were incubated with 10 µmol/L FITC-CTPSPFSHC (SEQ ID NO:2) or FITC-CVQTAQLLC (SEQ ID NO:3) for 1 hour at 37° C., washed three times with PBS, fixed with 4% paraformaldehyde. Blood vessels were stained with mouse anti-human CD31 monoclonal antibody and Alexa Fluor 568 goat anti-mouse IgG as above described.

Figure 4B:
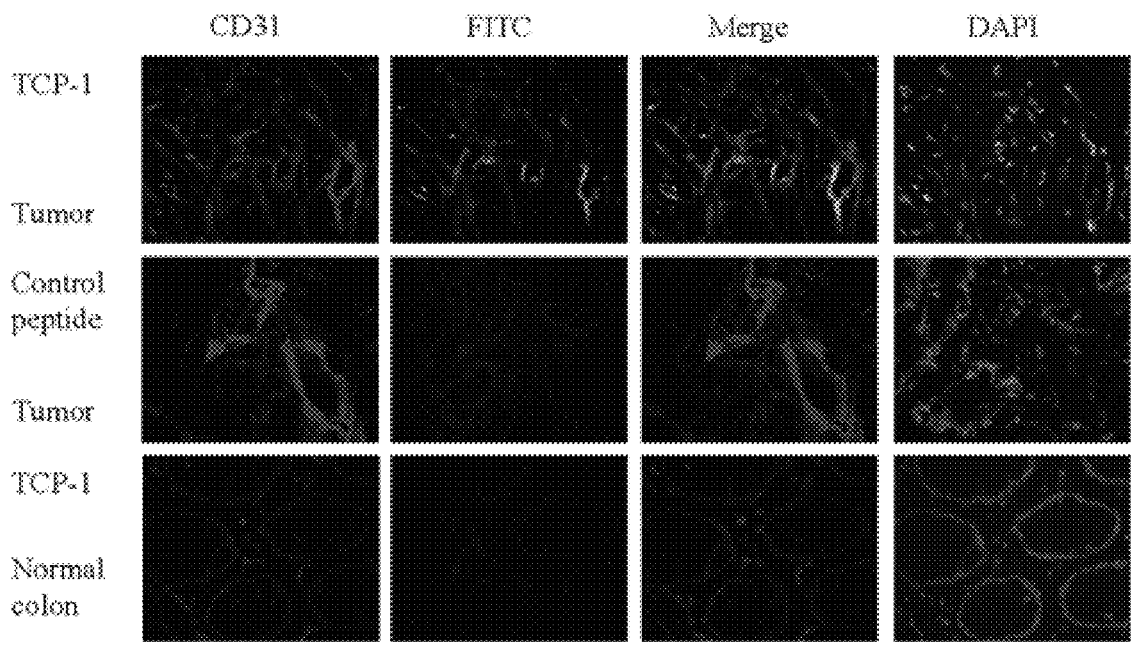

Results showed that FITC-labeled TCP-1 peptide bound to blood vessels of cancer tissues but not to vasculature of normal colon tissues. FITC-labeled control peptide did not interact with the blood vessels of either cancer or normal colon tissues (FIG. 4B). Fifty percent (5/10) of colon adenocarcinomas and fifty-five percent of rectal adenocarcinomas (6/11) from a total of 21 patients were found to be recognized by the peptide. The positive binding was usually found in tumor tissues at more advanced stages (in terms of lymphovascular permeation, T staging, N staging, and overall Dukes' staging).

Example 8

Therapeutic Treatment with CTPSPFSHC-GG-$_D$(KLAKLAK)$_2$

The following experiment was conducted to demonstrate the ability of TCP-1 to direct therapeutic agents to tumors of the alimentary canal. We conjugated TCP-1 with a pro-apoptotic peptide, $_D$(KLAKLAK)$_2$, which disrupts mitochondrial membranes upon receptor-mediated cell internalization and causes programmed cell death. This approach has been successfully employed for targeted apoptosis induction in angiogenic endothelial cells, tumor lymphatics and the vasculature of white fat. See: Zhang L, Giraudo E, Hoffman J A, Hanahan D, and Ruoslahti E (2006). Lymphatic zip codes in premalignant lesions and tumors. *Cancer Res* 66, 5696-5706; Kolonin M G, Saha P K, Chan L, Pasqualini R, and Arap W (2004). Reversal of obesity by targeted ablation of adipose tissue. *Nat Med* 10, 625-632; and, Ellerby H M, Arap W, Ellerby L M, Kain R, Andrusiak R, Rio G D, Krajewski S, Lombardo C R, Rao R, Ruoslahti E, et al. (1999). Anti-cancer activity of targeted pro-apoptotic peptides. *Nat Med* 5, 1032-1038. All-D enantiomer $_D$(KLAKLAK)$_2$ was used to avoid degradation by proteases. Ellerby H M, et al., (1999) Nat Med 5, 1032-1038.

Mice bearing orthotopic colorectal cancer were randomized into three groups. The therapeutic group was i.v. injected 260 µg/dose/mouse of the conjugated CTPSPFSHC-GG-D (KLAKLAK)$_2$ [CDK]. Control groups received an equimolar mixture of CTPSPFSHC (SEQ ID NO:1) and $_D$(KLAK-LAK)$_2$ [DKK], or PBS alone once every three days. Treatment was terminated 7 days after the first peptide administration as described in Kolonin M G, Saha P K, Chan L, Pasqualini R, and Arap W (2004). Reversal of obesity by targeted ablation of adipose tissue. *Nat Med* 10, 625-632 and Giordano R J, Landenranta J, Zhen L, Chukwueke U, Petrache I, Langley R R, Fidler I J, Pasqualini R, Tuder R M, and Arap W (2008). Targeted induction of lung endothelial cell apoptosis causes emphysema-like changes in the mouse. *J Biol Chem* 283, 29447-29460.

Tumors and control organs were dissected at the termination of the experiment. Histologic analysis was done to evaluate the density of tumor blood vessels. Apoptotic vascular endothelial cells were visualized by double staining with anticleaved caspase-3 and CD31 antibodies. (See Zhang L, Giraudo E, Hoffman J A, Hanahan D, and Ruoslahti E (2006). Lymphatic zip codes in premalignant lesions and tumors. *Cancer Res* 66, 5696-5706).

Figure 6:
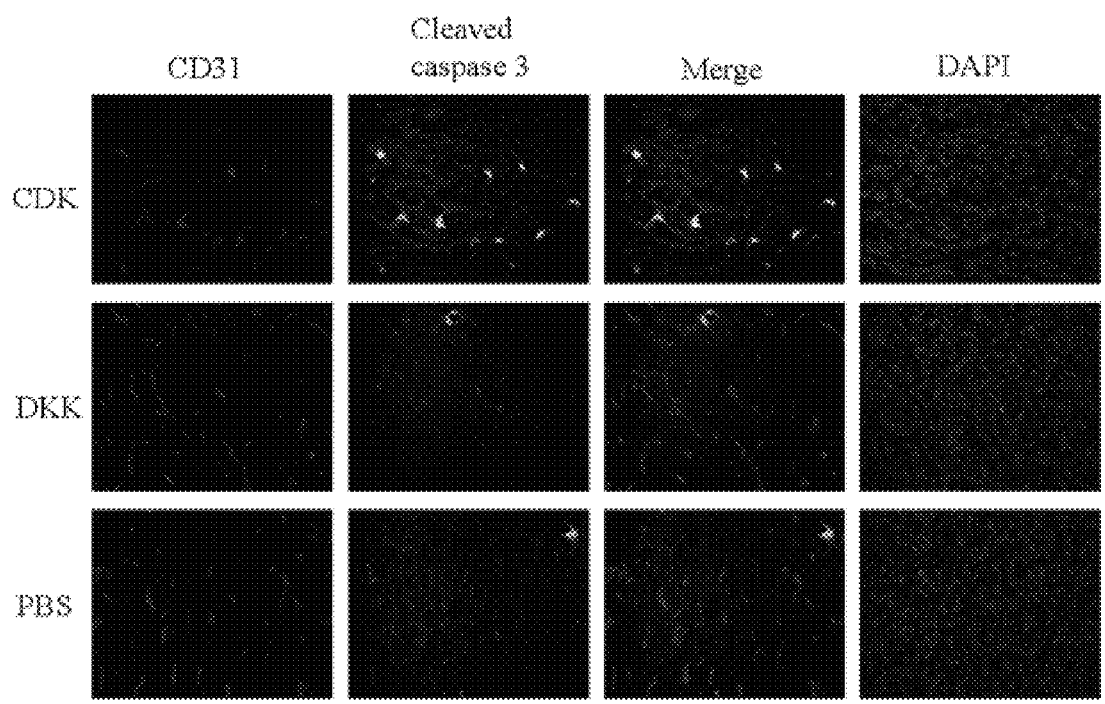
FIG. 6. describes the effect of TCP-1 coupled to an apoptotic peptide [TCP-GG-$_D$(KLAKLAK)$_2$] on caspase 3 cleavage. (A) Fluorograms describing pro-apoptotic activity (cleavage) with the coupled composition CDK versus uncoupled (DKK) and phosphate buffered saline; (B) quantification of apoptotic vasculature from treatment with coupled TCP-1; and, (C) examination for apoptotic vasculature in the normal colon tissues; (D) examination for apoptotic vasculature in brain tissues. CDK: TCP-GG-$_D$(KLAKLAK)$_2$, DKK: The mixture of TCP-1 and $_D$(KLAKLAK)$_2$.
Figure 6:
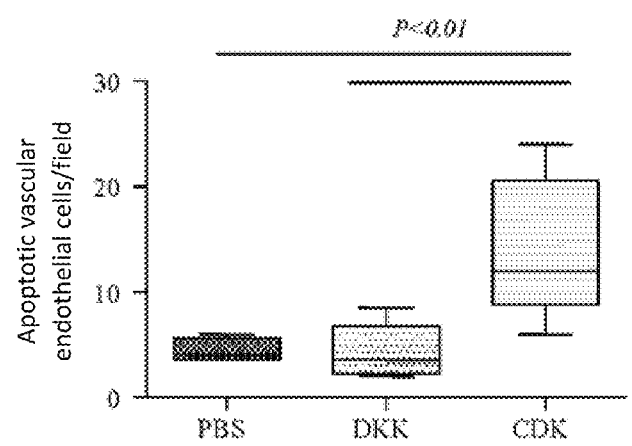
Figure 6:
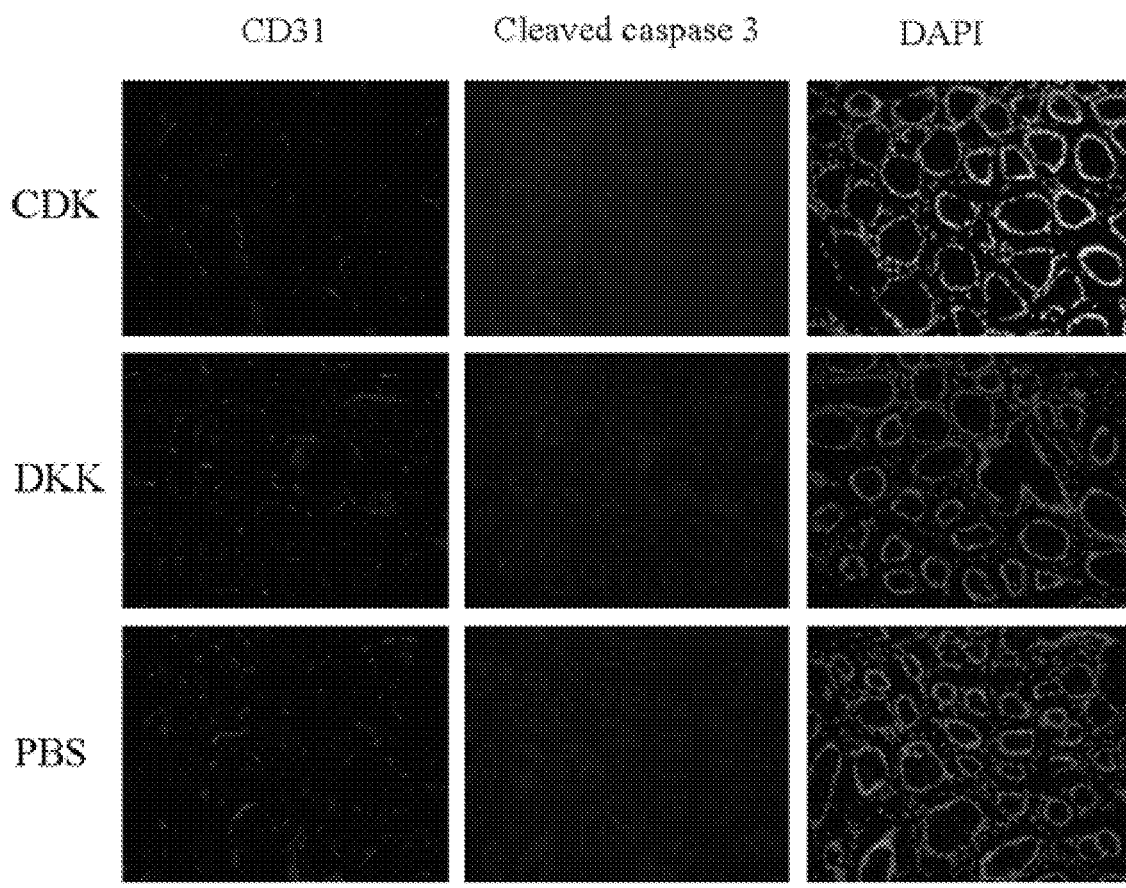
Figure 6:
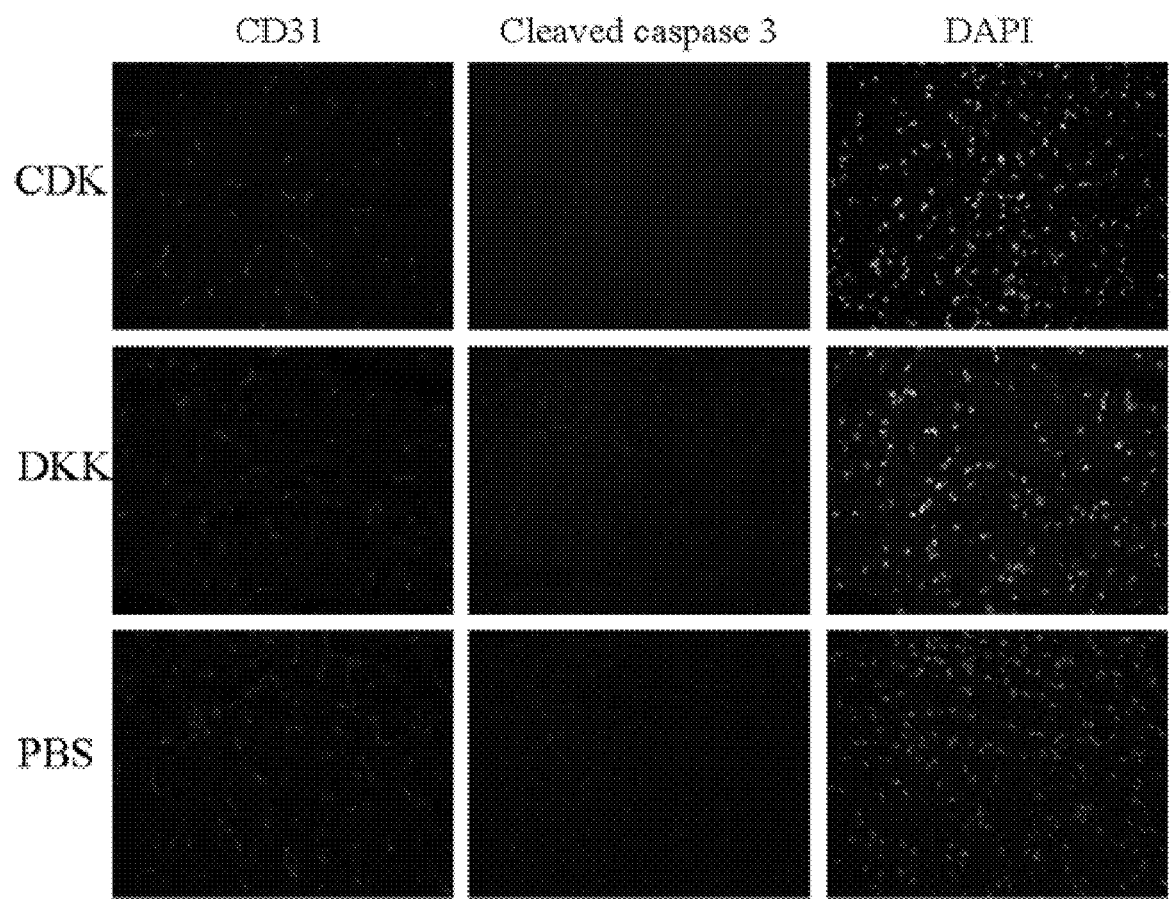

To determine the apoptosis of vasculature by the TCP-GG-$_D$ (KLAKLAK)$_2$, we examined the frequency of apoptosis in the vasculature by staining cleaved caspase 3 and vasculature marker CD31. Tumors of mice given TCP-GG-$_D$ (KLAKLAK)$_2$ had an obvious increase in vasculature endothelial cells expressing active caspase 3 compared with tumors of mice treated with PBS or a uncoupled mixture of TCP-1 and $_D$ (KLAKLAK)$_2$ (FIG. 6A). Accordingly, quantification of active caspase 3 revealed a remarkable increased number of apoptotic cells in the tumor vasculature of TCP-1 conjugate-treated mice when compared to the other two groups (FIG. 6B); in contrast, examination of apoptotic vasculature in the normal colon tissues and brain tissues showed hardly active caspase-3 positive cells among all of the three groups (FIGS. 6C and D).

Example 9

TCP-1 Binding to Human Gastric Tumors in an Orthotopic Gastric Cancer Mouse Model Human gastric cancer cells MKN45 were implanted in mice and the mice with the resulting tumors used to determine the homing ability of TCP-1 to human tumor induced vasculature.

Human gastric cancer cell line, MKN45, was purchased from the Human Science Research Resources Bank (Tokyo, Japan). MKN45 is a poorly differentiated human gastric adenocarcinoma cell line. The cell line was cultured at 37° C. in a humidified atmosphere containing 5% CO2, in RPMI-1640 medium (Invitrogen) supplemented with 2 g/L sodium bicarbonate, 100 units/ml penicillin (ICN Biomedicals, Costa Mesa, Calif.), 100 mg/ml streptomycin (ICN Biomedicals, Aurora, Ohio), pH 7.4 and 10% fetal bovine serum (FBS, Invitrogen).

The orthotopic gastric cancer model used male nude BALB/C mice 6~8 weeks of age. The mice were maintained at Chinese University of Hong Kong Animal Facility. The model was performed as previously published with some modifications. (See Shin V Y, Wu W K, Ye Y N, So W H, Koo M W, Liu E S, Luo J C, Cho C H. (2004, Carcinogenesis 25, 2487-2495). MNK45 cells were trypsinized, and the total cell number in the cell suspension was adjusted to 4×107 cells/ml. A volume of 100 µl of this cell suspension was inoculated into the gastric walls of mice. The mice were used after tumors grew for 3 weeks after implantation.

In addition, for a subcutaneous (s.c.) model, nude BALB/C mice 6~8 weeks of age were s.c. injected with 3×106 MKN45 cell at the right flank of nude mice. Mice were used after tumors grew for 3 weeks.

Other assays such as in vivo phage targeting assay, immunohistology, bio-distribution of the CTPSPFSHC-phage or FITC-labeled TCP-1 peptide, etc. refer to the orthotopic colorectal cancer model described above.

Figure 7:
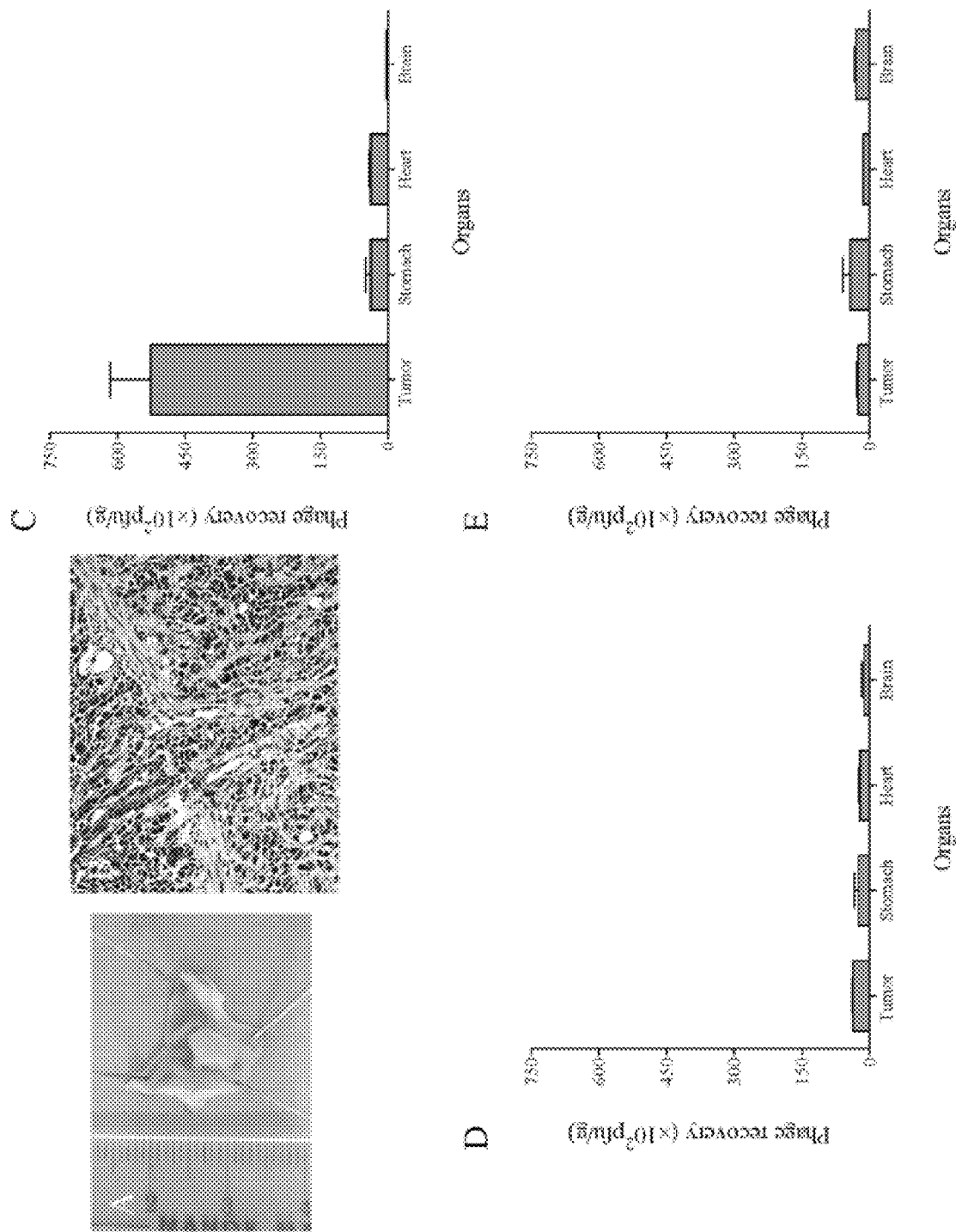
FIG. 7. describes (A and B) H&E staining of frozen sections from the tumor tissue to confirm tumor formation; (C and D) in vivo accumulation of homing phage versus insertless control phage to gastric tumors; and (E) TCP-1 homing phage's inability to selectively accumulate on subcutaneous (sc) tumors of MKN45 cells in the skin compared with orthotopic tumors in the stomach of nude mice.

After three weeks, we used H&E staining of paraffin sections from the tumor tissue confirmed the formation of gastric tumors (FIGS. 7A, B). CTPSPFSHC-phage or insertless control phage was intravenously injected into gastric cancer-bearing mice. Both tumor tissue and normal control organs were collected and assayed for phage accumulation. CTPSPFSHC-phage was enriched from 14 to 115-fold higher in tumor tissue than in control organs including normal stomach, heart and brain (FIG. 7C). Insertless control phage hardly showed selectivity to tumor tissue and normal control organ (FIG. 7D). Meanwhile we also found that the CTPSPFSHC-phage homed less efficiently to s.c. tumor of MKN45 cells in the skin than to orthotopic tumor in the stomach in nude mice of the same cell line (FIG. 7E).

Figure 8:
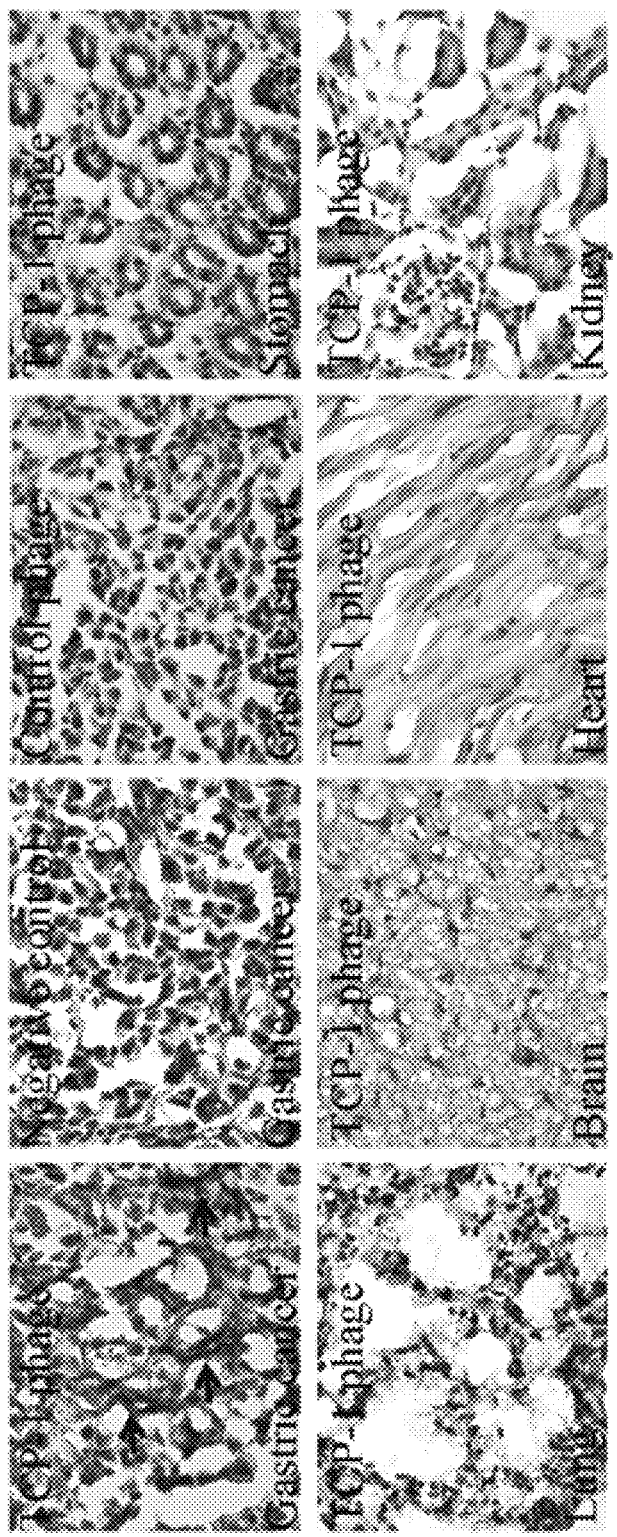
FIG. 8. describes frozen sections of tumor tissue and control organs to demonstrate that CTPSPFSHC-phage was localized in gastric cancer tissues, but not control organs.
Figure 9:
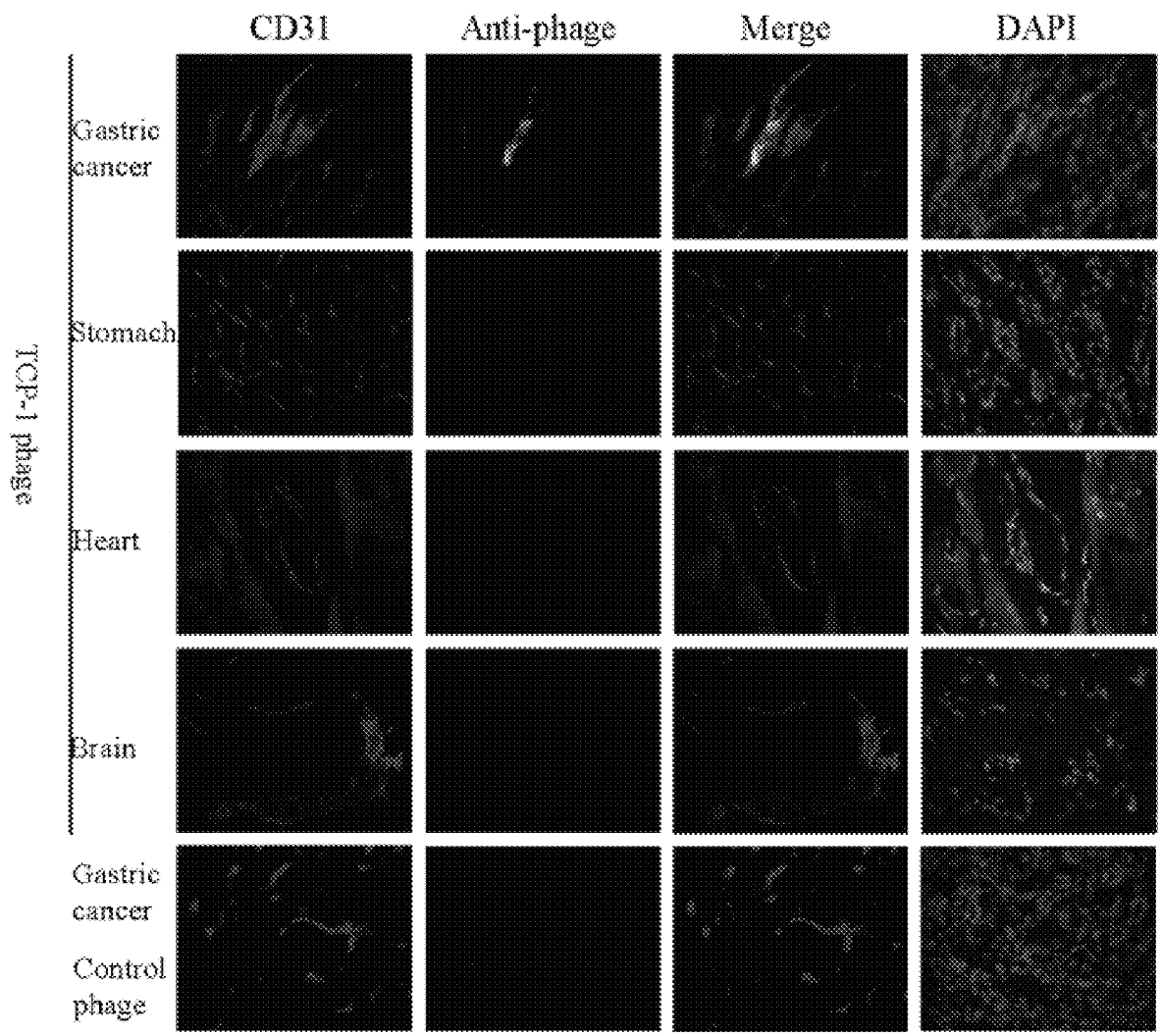
FIG. 9. describes CTPSPFSHC-phage colocalised with CD-31 positive endothelial cells in gastric cancer tissues but not with the vessels in control organs FIG. 10. describes frozen sections of tumor and control tissue Blood vessels were stained by CD31 antibody conjugated Alexa-568 and with FITC-labeled TCP-1.

To investigate the bio-distribution of CTPSPFSHC-phage, we first performed the immuno-histochemistry (DAB development) with the Fd anti-phage antibody after intravenous injection. Tumor tissue and control organs were removed and prepared frozen sections. The CTPSPFSHC-phage was found to localize in gastric cancer tissues, but not control organs such as heart, brain and normal stomach tissues, etc (FIG. 8). Insertless phage was not detectable in the gastric cancer tissues (FIG. 8). Subsequently, double label immunofluorescent staining (described above in Example 1) was used to visualize the colocalization of phage (anti-phage antibody) and vasculature (CD31 antibody). CTPSPFSHC-phage colocalised with CD-31 positive endothelial cells in gastric cancer tissues but not with the vessels in control organs (FIG. 9). Insertless phage was not detectable in the vasculature of tumor tissues (FIG. 9 bottom).

To further confirm whether the selective phage homing was due to the CTPSPFSHC (SEQ ID NO:1) peptide (TCP-1), chemically synthetic FITC-conjugated TCP-1 or control peptide was intravenously injected into gastric cancer-bearing mice to study the location of the peptide. Biodistribution of fluorescein-conjugated peptides was examined after i.v. injection of the peptide (300 nmol in 300 µl PBS) into the tail vein of a gastric cancer-bearing mouse. The peptide was allowed to circulate for 1 hour.

Figure 10:
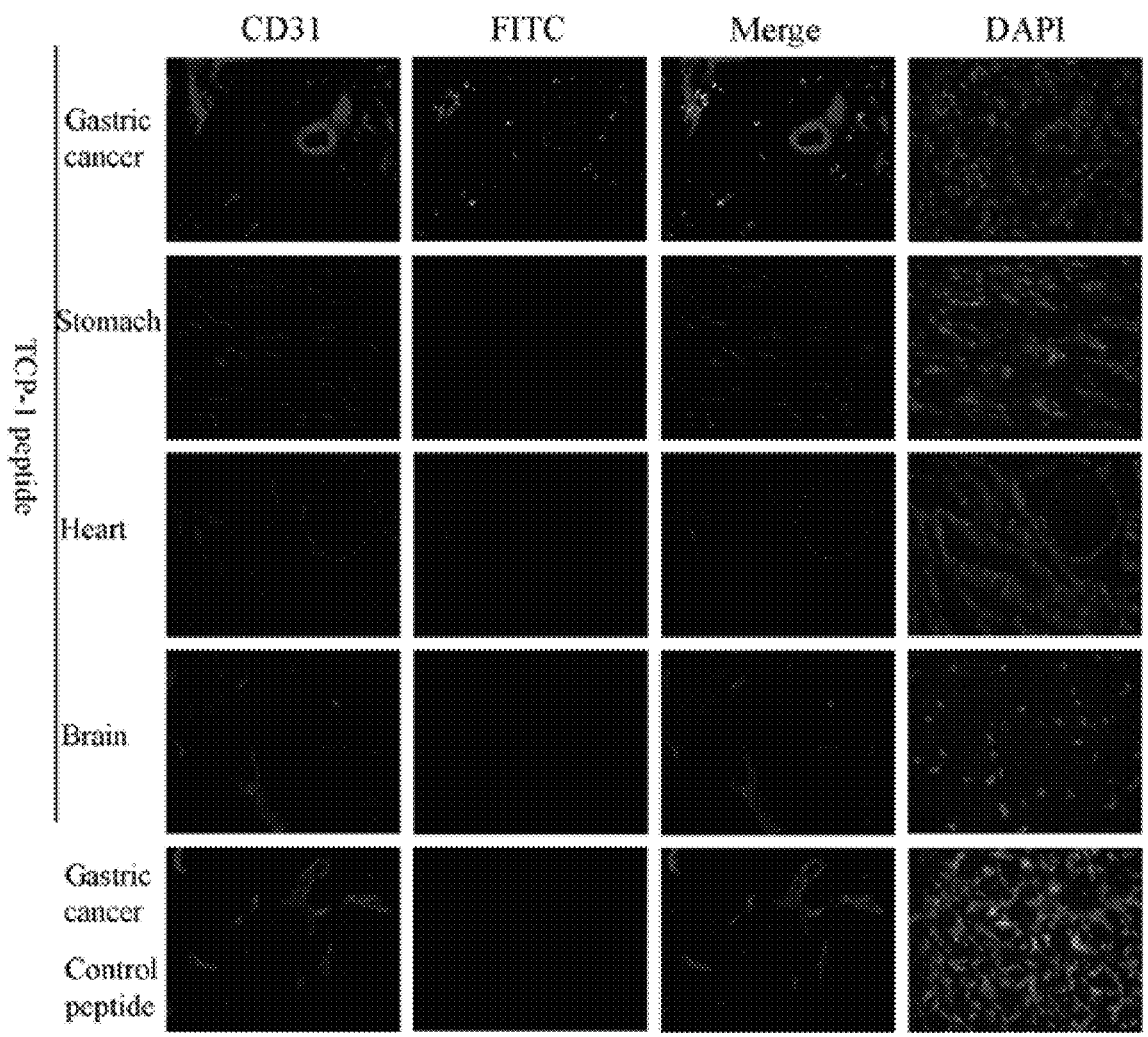

Tumor and control tissues were collected and frozen sections prepared as described above. Blood vessels were stained by CD31 antibody (secondary antibody conjugated Alexa-568). The FITC-labeled TCP-1 colocalised with CD31 in the tumor tissues (FIG. 10). But it was not detectable in control organs (FIG. 10). FITC-labeled control peptide was not found in the tumor tissues (FIG. 10 bottom). Taken together with the immunolocalization analyses of TCP-1 phage homing, the peptide localization data confirmed that TCP-1 peptide also homed specifically to blood vessels in gastric cancer tissues but not to the vasculature of control organs.

TABLE 1

Sequences Disclosed

| Sequence | Function | SEQ ID NO: |
|---|---|---|
| CTPSPFSHC | TCP-1 | 1 |
| CTPSPFSHC-GG-$_D$(KLAKLAK)$_2$ | TCP-1 linked to an apoptosis inducing peptide | — |
| KLAKLAK | Apoptosis inducing peptide | 6 |
| CVQTAQLLC | Control peptide | 7 |

Example 10

Binding and Internalization of TCP-1 Phage in the Colon 26 and SW1116

Cell lines and cell culture: The murine colorectal cancer cell colon 26, human colon cancer cell SW1116 were cultured at 37° C. in a humidified atmosphere containing 5% $CO_2$, in RPMI-1640 medium supplemented with 2 g/L sodium bicarbonate, 100 units/ml penicillin, 100 mg/ml streptomycin and 10% FBS.

Cell binding and internalization assay: Cells were grown in specific Petri dish for confocal imaging (Corning, US) for 24 h, washed twice with PBS, incubated with $1 \times 10^9$ pfu of CTPSPFSHC-phage (TCP-1 phage) or control phage in 1% FBS in RPMI 1640 for 4 h at 37° C., and washed five times with PBS and two times with 150 mM NaCl, 20 mM glycine, pH 2.2, to remove cell surface binding phage. Cells were washed with PBS, fixed with 4% paraformaldehyde (PFA) in PBS for 15 min, washed with PBS, permeabilized with 0.2% Triton X-100, washed with PBS, and blocked with 10% normal goat serum for 1 h at room temperature. Cells were then incubated with a 1:100 dilution of the anti-M13 phage antibody in 10% normal goat serum at 4° C. overnight, washed with PBS, and incubated with a 1:800 dilution of Alexa Fluor 488 goat anti-rabbit IgG in 10% normal goat serum for 1 h at room temperature. Finally, cells were washed with PBS, fixed with 4% PFA in PBS, mounted, and visualized under a confocal microscope.

Figure 11:
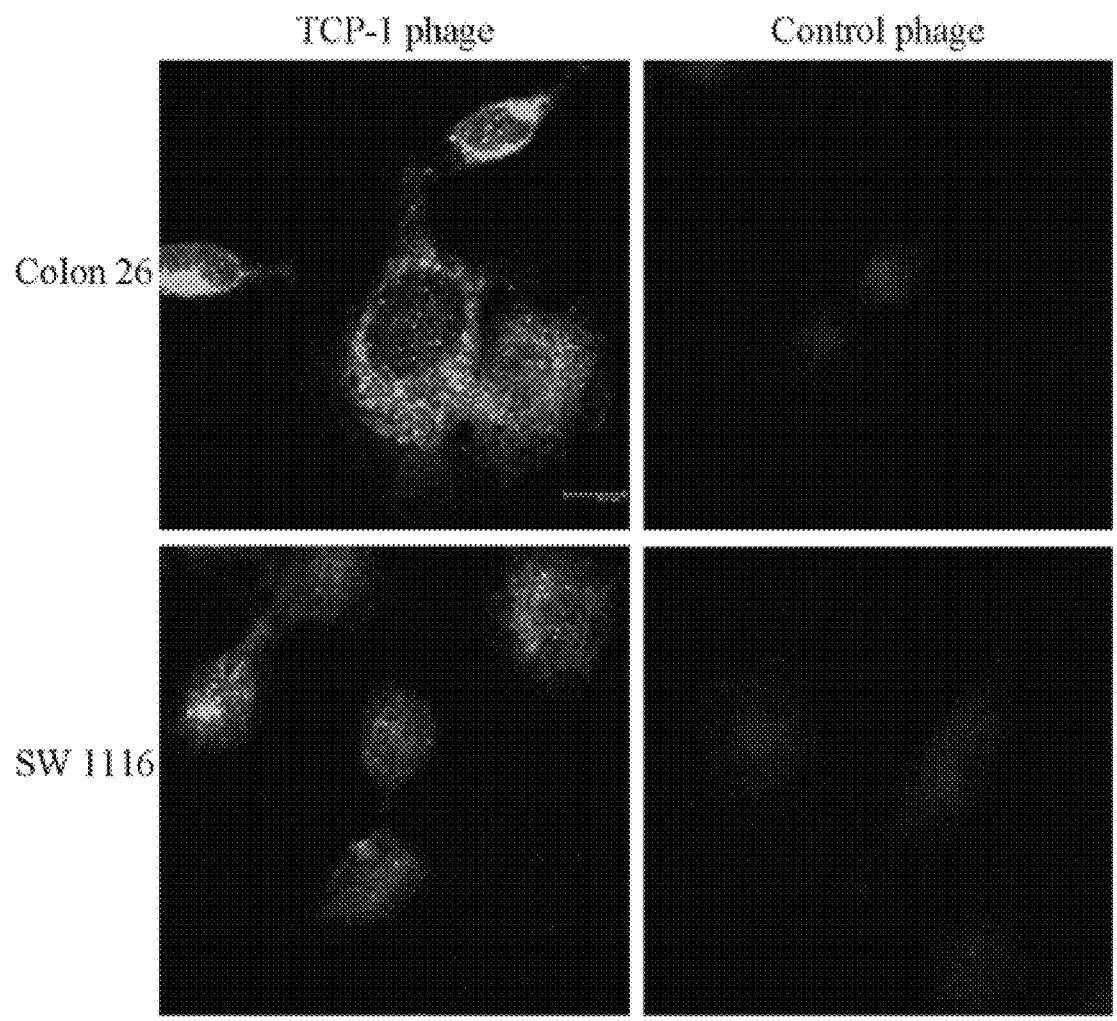
FIG. 11. TCP-1 phage can internalize into the colon cancer cells in vitro.

Binding and internalization of TCP-1 phage in the colon 26 and SW1116: To evaluate whether the TCP-1 peptide displayed on the phage surface could bind to cancer cells and is internalized into cancer cells, TCP-1 phage or control phage was incubated with colon 26 and SW1116 cells for 4 h at 37° C. Surface bound phage was removed by elute buffer (pH=2.2), cells were then permeabilized and stained with anti-phage antibody. An Alexa 488-conjugated secondary antibody was used to detect the localization of phage particles. We found that TCP-1 phage can interact with colon 26 and SW1116 cells and be internalized into these two cell lines (FIG. 11). Control phage particles were not detectable except for background staining (FIG. 11).

Example 11

TCP-1 Conjugate and Induction of Apoptosis in Colorectal Cancer Cells

Cell lines and cell culture: The murine colorectal cancer cell colon 26, human colon cancer cell SW1116 were cultured at 37° C. in a humidified atmosphere containing 5% $CO_2$, in RPMI-1640 medium supplemented with 2 g/L sodium bicarbonate, 100 units/ml penicillin, 100 mg/ml streptomycin and 10% FBS.

In vitro cell viability assay (MTT assay): Cell viability was assessed by MTT assay, which depends on the ability of viable cells to reduce the MTT to a colored formazan product. In brief, cells ($10^4$ cells per well) were seeded in 96-well microculture plates overnight for attachment, and then incubated with increasing concentrations of the peptides CTPSPFSHC-GG-$_D$(KLAKLAK)$_2$ or CTPSPFSHC (SEQ ID NO:1) or $_D$(KLAKLAK)$_2$ in 100 µl of 1% FBS in DMEM for 6~48 hours at 37° C. In the next step, MTT was added to each well, and the cells were further incubated for 3 h. The colored formazan product was determined photometrically at 570 nm in a multi-well plate reader (Bio-Rad).

Figure 12:
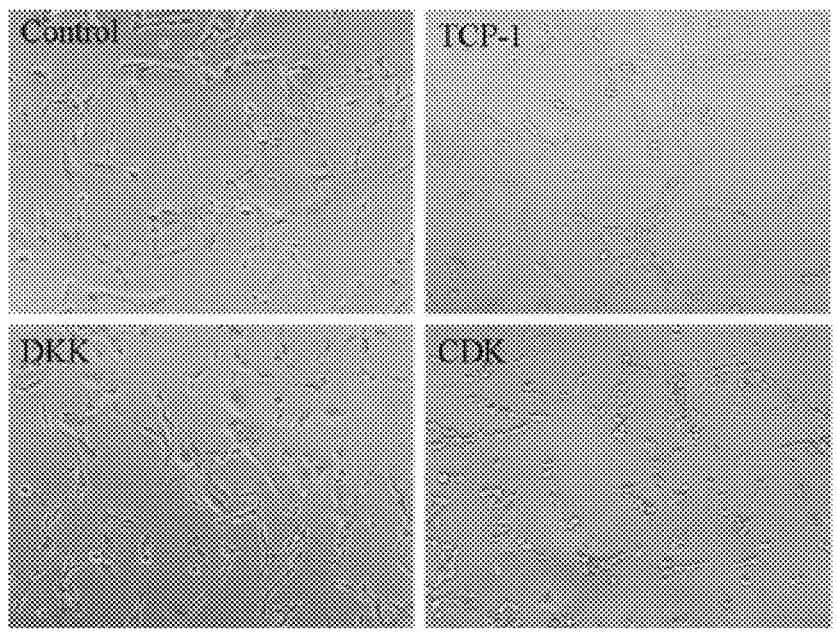
FIG. 12. TCP-1 can enhance the apoptotic action of a pro-apoptotic peptide on mouse colon cancer cells in vitro. (A) Morphological changes associated with cell death after exposure to TCP-1 conjugate; (B) Cell viability of colon 26 cell was inhibited by TCP-1 conjugate. CDK: TCP-GG-$_D$(KLAKLAK)$_2$, DKK: $_D$(KLAKLAK)$_2$.
Figure 12:
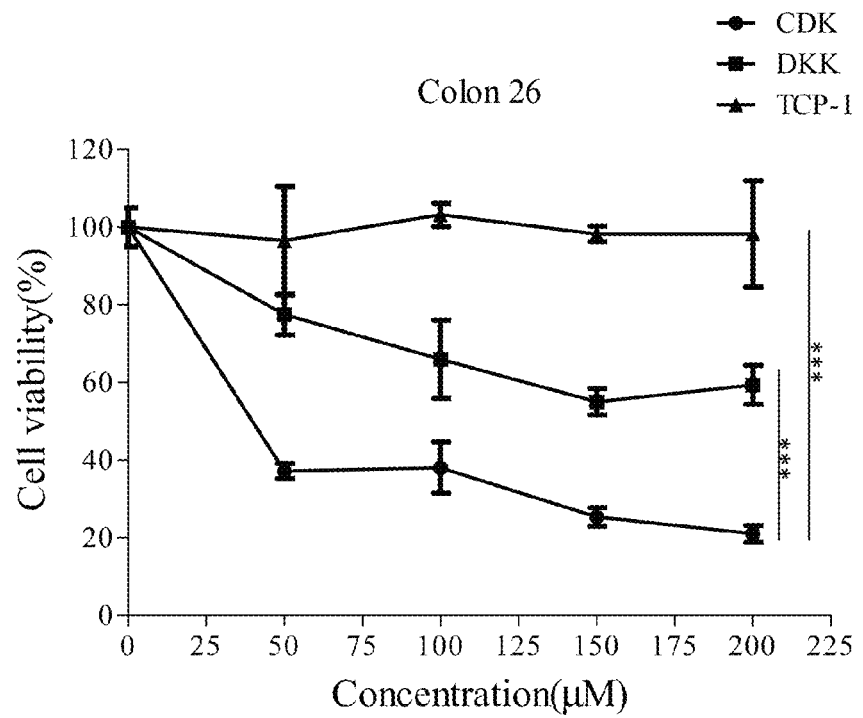
Figure 13:
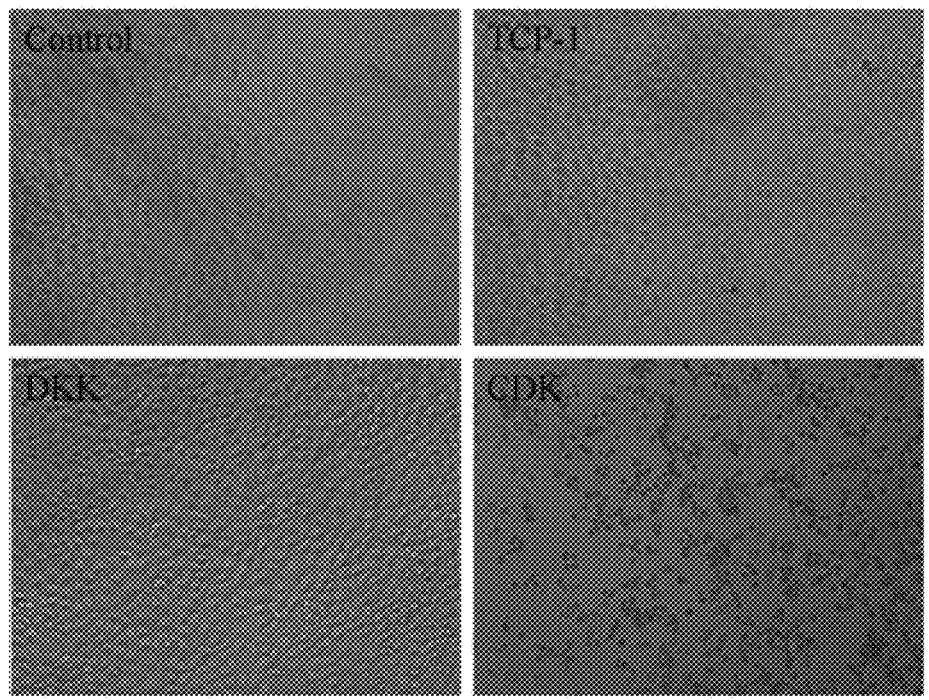
FIG. 13. TCP-1 can enhance the apoptotic action of a pro-apoptotic peptide on human colon cancer cells in vitro. (A) Morphological changes associated with cell death after exposure to TCP-1 conjugate; (B) Cell viability of SW1116 cell was inhibited by TCP-1 conjugate. CDK: TCP-GG-$_D$(KLAKLAK)$_2$, DKK: $_D$(KLAKLAK)$_2$.
Figure 13:
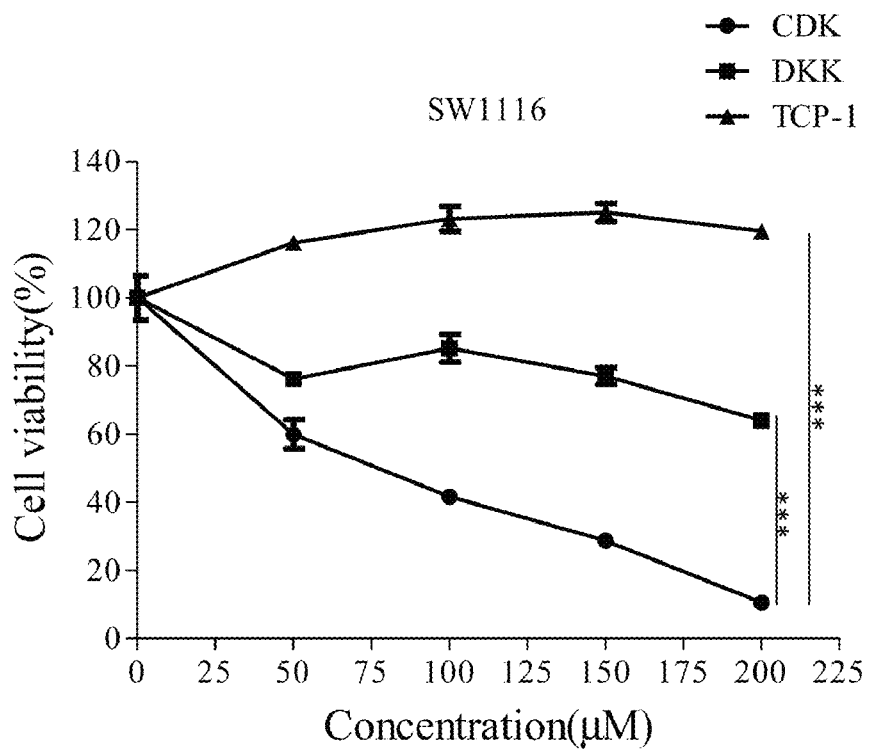

TCP-1 conjugate and induction of apoptosis in colorectal cancer cells: Next, in order to examine whether the TCP-1 peptide could serve as a drug carrier into cancer cells, we synthesized a chimeric peptide of TCP-1 peptide to a proapoptotic peptide $_D$(KLAKLAK)$_2$, which disrupts mitochondrial membranes upon receptor-mediated cell internalization and causes programmed cell death. Increasing concentrations of TCP-1 conjugate (TCP-GG-$_D$(KLAKLAK)$_2$), equimolar TCP-1 or $_D$(KLAKLAK)$_2$ were incubated with colon 26 or SW1116 cells at 37° C. Cell viability was assessed after 6 h (colon 26) and 48 h (SW1116). The effect of TCP-1 conjugate on the cell viability was determined and compared respectively with TCP-1 or $_D$(KLAKLAK)$_2$ alone. TCP-1 conjugate inhibited the proliferation of colon 26 and SW1116 cells more efficiently than $_D$(KLAKLAK)$_2$ alone, whereas no significant effect on cell viability was observed for TCP-1 alone in concentration-dependent manner (FIGS. 12 and 13). The non-conjugated peptide TCP-1 revealed no detectable toxic effects on the two cell lines, but non-conjugated peptide $_D$(KLAKLAK)$_2$ could be detected a much weaker toxic effects on these two cell lines when compared with TCP-1 conjugate, which might be due to non-specific uptake of $_D$(KLAKLAK)$_2$ by colorectal cancer cells.

FIGS. 12A and 13A show the morphological changes associated with cell death after exposure to TCP-1 conjugate. The cells were incubated with 200 µM TCP-1 conjugate, $_D$(KLAKLAK)$_2$, or TCP-1 for 6 h (colon 26) or 48 h (SW1116). Morphological changes were recorded. CDK: TCP-1 conjugate, DKK: $_D$(KLAKLAK)$_2$, original magnification: 200×. 12B and 13B show the cytotoxic effects of TCP-1 conjugate on colon 26 cells and SW1116. All experiments were performed in triplicate. P<0.001).

Example 12

Toxicity of TCP-1 Peptide in Mice

Materials and Methods

Animal: This study was approved by the Laboratory Animals Ethics Committee of the Chinese University of Hong Kong. Male BALB/c mice aged 9 weeks were used in this study. They were maintained at the Chinese University of Hong Kong Animal Facility. All animals were housed in plastic cages (four or five mice/cage) with free access to drinking water and a pelleted basal diet, under controlled conditions of humidity (50±10%), light (12/12 h light/dark cycle) and temperature (23±2° C.).

Treatment and sample preparations: Animals were randomly divided into two groups (five mice/group) with similar body weight distributed at the beginning of the experiments. The experimental group was i.v. injected with 100 µg/dose/mouse of TCP-1 peptide and the control group received an equal volume of PBS alone once every other days. Treatment was terminated 16 days after the first dose of peptide administration.

Animals were euthanized 2 days after the last injection by sodium pentobarbital. Blood samples were collected via the abdominal aorta from the animals. They were used for hematological examination and blood biochemical assay. Organs including heart, brain, lung, colon, liver, spleen and kidney were collected and fixed in 10% formalin solution for histological analysis.

Hematologic studies: Hematological examinations were performed using an automatic blood cell counter (Sysxem KX-21, Japan) for the erythrocyte count (RBC), white blood cell count (WBC), hemoglobin (HGB) and platelet count (PLT).

Biochemical studies: Plasma was harvested from blood samples. Biochemical determinations were carried out with a clinical automatic biochemical analyzer (HITACHI 7020, Japan) for alanine aminotransferase (ALT), lactic dehydrogenase (LDH), total protein (TP), albumin (ALB), urea nitrogen (BUN) and creatinine (CREA) levels.

Histological examinations: The tissues collected above were fixed in 4% buffered formalin overnight. They were then treated according to the routine histological procedures. Afterward, tissues were embedded into paraffin blocks. Sections of 5 µm in thickness were cut with a microtome (American Optical Corporation, USA), prepared on glass slides using the water floatation method.

Sections were subsequently stained by Harris hematoxylin solution and eosin Y solution (H & E). The slides were finally mounted with xylene based mounting medium. Based on the H&E staining, histological assessments were performed by a board-certified pathologist in a blinded manner according to the criteria previously reported.

Statistical analysis: The data are presented as mean±SEM. The significance of difference between control and treated groups for body weight, hematology and blood biochemistry was analyzed by Student's t test. P<0.05 was considered statistical difference.

Results

Figure 14:
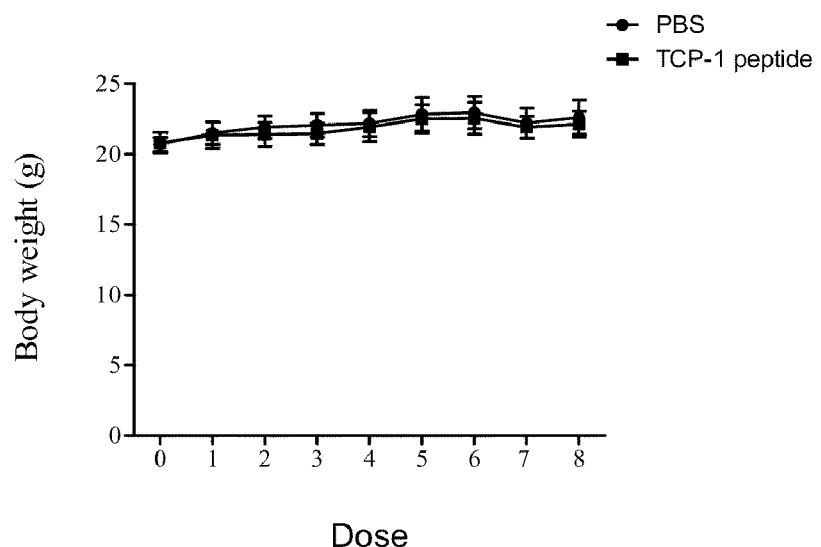
FIG. 14. Changes of body weight in mice treated with TCP-1 peptide (100 µg/mouse) given i.v. once every other day for a total of 8 doses.

Body weight: Firstly, body weight was recorded in this study before every injection. Compared with the PBS control group, there was no significant body change in the peptide-treated group (FIG. 14).

Figure 15:
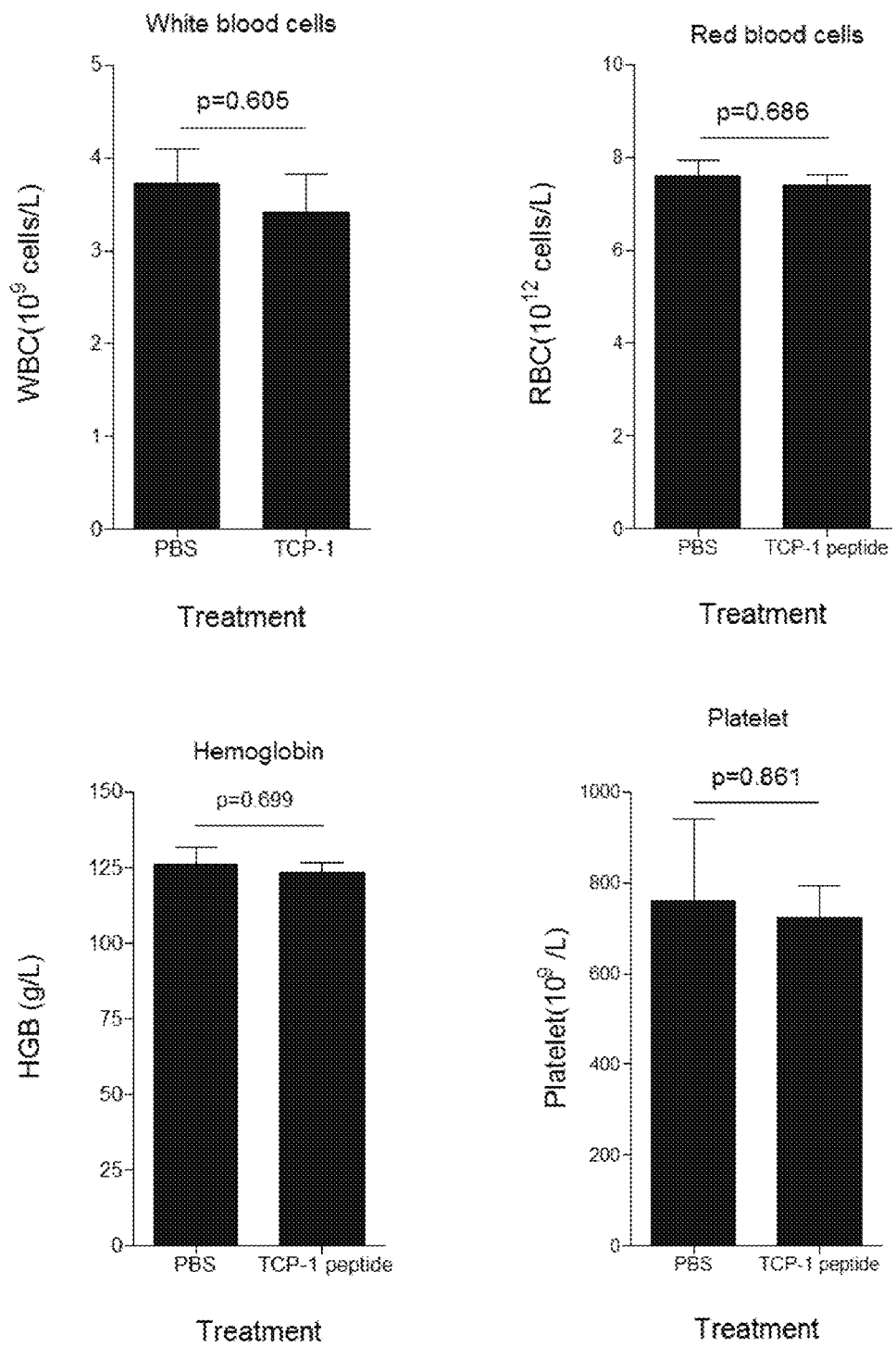
FIG. 15. Effect of TCP-1 on hematological parameters measured after 8 doses of TCP-1 injections (i.v. 100 µg/mouse) in mice.

Hematological results: When compared with the PBS control group, no significant changes were found in the peptide-treated group in the four hematological parameters including red blood cell count (RBC), white blood cell count (WBC), hemoglobin (HGB) and platelet count (PLT) (FIG. 15). The results implicated that TCP-1 peptide treatment for 8 consequent doses did not cause any hematological disorders.

Figure 16:
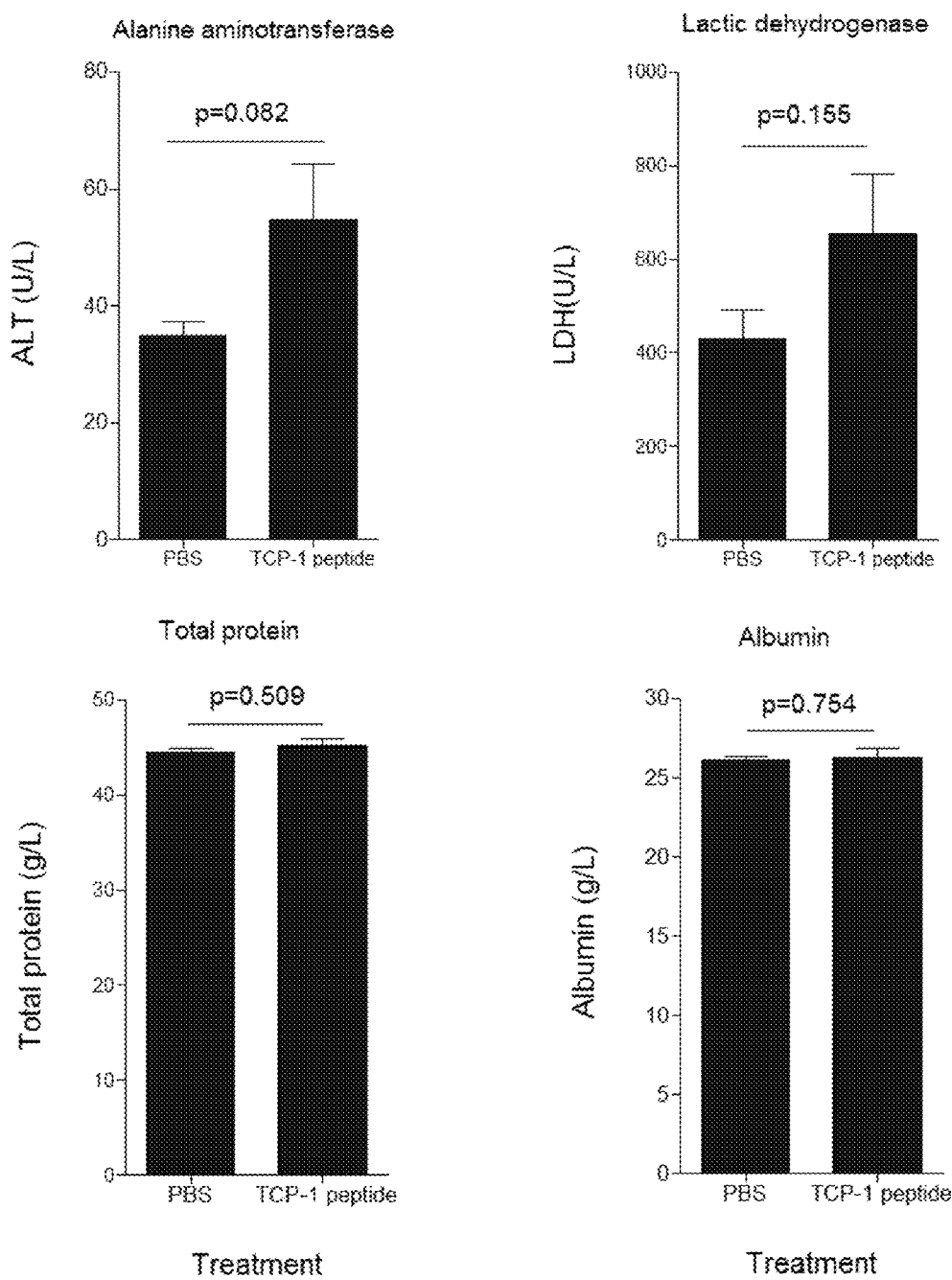
FIG. 16. Effect of TCP-1 on liver function measured after 8 doses of TCP-1 injections (i.v. 100 µg/mouse) in mice.

Biochemical results: To assess any toxicological effects of TCP-1 on liver functions, levels of ALT, LDH, TP and ALB were examined. Although the ALT and LDH levels in the peptide-treated mice appeared a light elevation, changes were minimal and carried no statistical significance. The values of TP and ALB were almost equal in the two groups. The data suggest that 8-dose injections of TCP-1 peptide did not adversely affect the liver function (FIG. 16).

Figure 17:
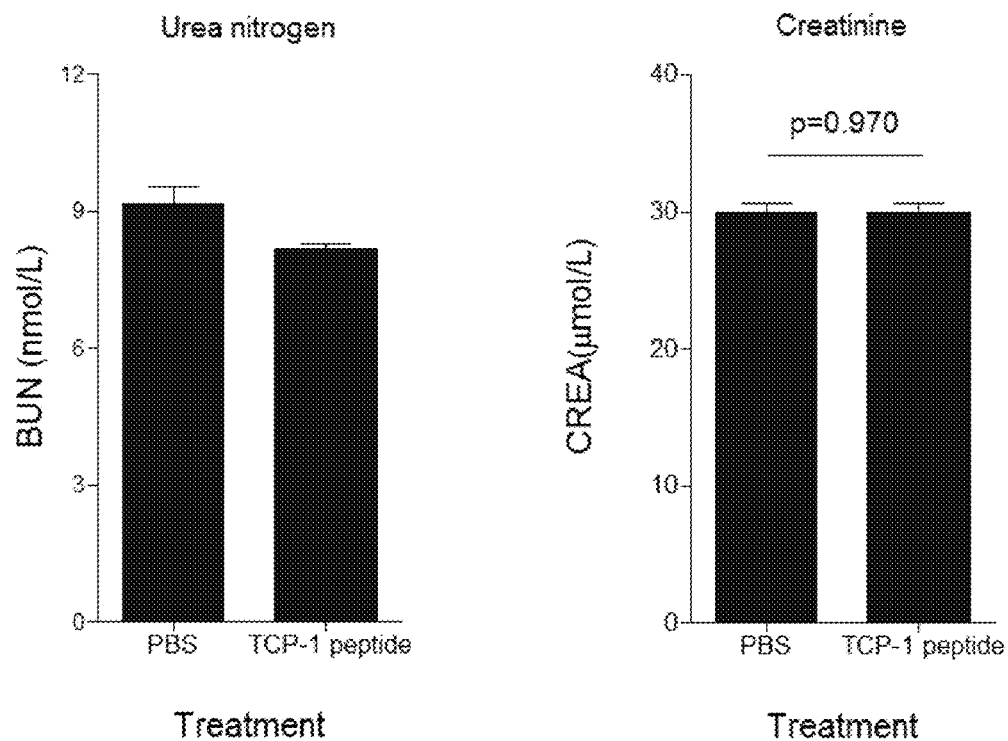
FIG. 17. Effect of TCP-1 on renal function measured after 8 doses of TCP-1 injections (i.v. 100 µg/mouse) in mice.

On the other hand, the blood BUN and CREA levels were investigated for renal function. In our study, 8-dose injections of TCP-1 peptide had almost no effect on the values of BUN and CREA as compared to the control group, indicating that TCP-1 peptide has no toxicity against kidney (FIG. 17).

Figure 18:
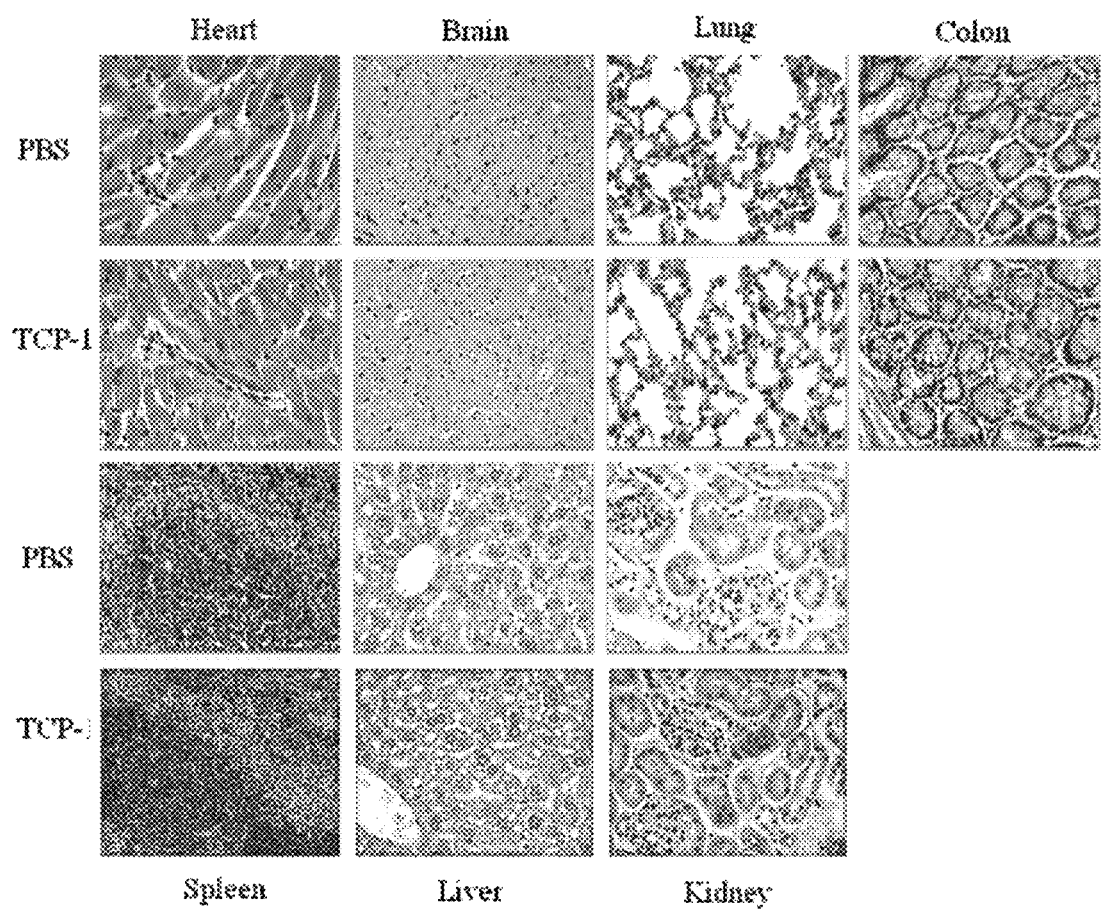
FIG. 18. Histological examination in mice treated with 8 doses of TCP-1 injections (i.v. 100 µg/mouse) in mice.

Histological examination: Tissue sections from different organs including heart, brain, lung, colon, kidney, liver and spleen were analyzed by a board-certified pathologist after H & E staining. There were no detectable pathological changes in the two groups, suggesting that TCP-1 did not produce any pathological changes in these organs after 8 doses of TCP-2 injections (FIG. 18).

What is claimed is:

1. An alimentary tumor vascular homing protein comprising at least one copy of a domain consisting of CTPSPFSHC (SEQ ID NO:1).

2. A homing protein of claim 1 having a molecular weight of between 1 and 100 kDa.

3. A homing protein of claim 1 having between 2 and 10 copies of the domain CTPSPFSHC (SEQ ID NO:1).

4. A homing protein of claim 1 in a pharmaceutically acceptable composition.

5. A homing protein of claim 4 in a sterile aqueous liquid having a pH of between 6 and 8.

6. A homing protein of claim 4 in a lyophilized powder.

7. A homing protein of claim 4 in a sterile aqueous liquid.

8. A homing protein of claim 1 fused to detectable moiety.

9. A homing protein of claim 8 wherein the detectable moiety is selected from the group consisting of fluorophore, a radioopaque dye, a magnetic imaging contrast agent and a radiolabel.

10. A homing protein of claim 8 wherein the detectable moiety is fused to the homing protein via a covalent bond.

11. A homing protein of claim 8 wherein the detectable moiety is linked to the homing protein via an ionic bond.

12. A homing protein of claim 1 fused to a therapeutic agent.

13. A homing protein of claim 12 where the therapeutic agent is an anti-cancer agent is selected from the group consisting of alkylating agents, bifunctional alkylating agents, non-steroidal aromatase inhibitors, immunotherapeutic agents, nitrosourea compounds, antimetabolites, antitumor antibiotics, mitotic inhibitors, radiation, topoisomerase I inhibitors, and anti-estrogens.

14. A method of detecting tumor-induced vasculature in the alimentary canal of a mammal said method comprising:
 i. contacting the alimentary canal of the mammal hosting a solid tumor surrounded by tumor-induced vasculature with an amount of an alimentary tumor vascular homing protein comprising at least one copy of a domain consisting of CTPSPFSHC (SEQ ID NO:1) said protein linked to a detectable moiety where the amount is sufficient to detect the tumor-induced vascular tissue surrounding the tumor; and,
 ii. detecting the homing protein in the tumor-induced vascular tissue.

15. A method of claim 14 where the detectable moiety is selected from the group consisting of fluorophore, a radioopaque dye, a magnetic imaging contrast agent and a radiolabel.

16. A method of claim 14 where the contacting is via intravenous administration.

17. A method of claim 14 where the tumor-induced vasculature is in the intestine.

18. A method of reducing the solid tumor load of a patient hosting a solid tumor located in its alimentary canal and surrounded by tumor-induced vasculature, said method comprising:
 administering an amount of a therapeutic agent comprising:
  i. an alimentary tumor vascular homing protein comprising at least one copy of a domain consisting of CTPSPFSHC (SEQ ID NO:1); and,
  ii. an anti-cancer agent capable of reducing the tumor load of the patient;
 wherein the homing protein is linked to the biologically active moiety; and,
 wherein the amount of therapeutic agent administered is sufficient to reduce the tumor load of the patient.

19. A method of claim 18 where the tumor is a carcinoma.

20. A method of claim 18 where the anti-cancer agent is selected from the group consisting of: alkylating agents, bifunctional alkylating agents, non-steroidal aromatase inhibitors, immunotherapeutic agents, nitrosurea compounds, antimetabolites, antitumor antibiotics, mitotic inhibitors, radiation, topoisomerase I inhibitors, and anti-estrogens.

21. A method of claim 18 where the tumor is located in the stomach or intestine.

22. A method of claim 18 where the therapeutic agent is administered orally or intravenously.

* * * * *